(12) United States Patent  
Herzinger et al.

(10) Patent No.: US 8,248,607 B1  
(45) Date of Patent: Aug. 21, 2012

(54) EMPIRICAL CORRECTION FOR SPECTROSCOPIC ELLIPSOMETRIC MEASUREMENTS OF ROUGH OR TEXTURED SURFACES

(75) Inventors: Craig M. Herzinger, Lincoln, NE (US); Blaine D. Johs, Lincoln, NE (US); Mathias M. Schubert, Lincoln, NE (US); Tino Hofmann, Lincoln, NE (US)

(73) Assignees: J.A. Woollam Co., Inc., Lincoln, NE (US), part interest; Board of Regents of Nebraska University, Lincoln, NE (US), part interest ( * ) Notice: Subject to any disclaimer, the term of this patent is extended or adjusted under 35 U.S.C. 154(b) by 214 days.

(21) Appl. No.: 12/804,958

(22) Filed: Aug. 3, 2010

Related U.S. Application Data

(60) Provisional application No. 61/273,372, filed on Aug. 4, 2009.

(51) Int. Cl.  
*G01J 4/00* (2006.01)

(52) U.S. Cl. .................... 356/369; 356/368

(58) Field of Classification Search ........... 438/7, 16; 356/369, 364, 237.1–237.5, 368; 250/559.09, 250/225  
See application file for complete search history.

(56) References Cited

U.S. PATENT DOCUMENTS

| | | | | |
|---|---|---|---|---|
| 4,097,110 A | | 6/1978 | Carey | 350/149 |
| 4,373,817 A | * | 2/1983 | Coates | 356/636 |
| 5,045,704 A | * | 9/1991 | Coates | 250/372 |
| 5,303,709 A | | 4/1994 | Dreher | 128/665 |
| RE34,783 E | * | 11/1994 | Coates | 250/372 |
| 5,412,473 A | | 5/1995 | Rosencwaig et al. | 356/451 |
| 5,486,701 A | * | 1/1996 | Norton et al. | 250/372 |
| 5,596,411 A | * | 1/1997 | Fanton et al. | 356/369 |
| 5,608,526 A | * | 3/1997 | Piwonka-Corle et al. | 356/369 |
| 5,771,094 A | | 6/1998 | Carter et al. | 356/326 |
| 5,787,890 A | | 8/1998 | Reiter et al. | 128/665 |
| 5,798,837 A | * | 8/1998 | Aspnes et al. | 356/369 |
| 5,835,222 A | * | 11/1998 | Herzinger | 356/369 |
| 5,889,593 A | * | 3/1999 | Bareket | 356/445 |
| 5,900,939 A | * | 5/1999 | Aspnes et al. | 356/369 |
| 5,910,842 A | * | 6/1999 | Piwonka-Corle et al. | 356/369 |
| 5,956,147 A | | 9/1999 | Jellison, Jr. et al. | 356/369 |
| 6,091,499 A | * | 7/2000 | Abraham et al. | 356/623 |
| 6,112,114 A | | 8/2000 | Dreher | 600/476 |
| 6,600,560 B2 | * | 7/2003 | Mikkelsen et al. | 356/369 |
| 6,693,711 B1 | | 2/2004 | Leger et al. | 356/369 |
| 6,798,511 B1 | | 9/2004 | Zhan et al. | 356/369 |
| 6,822,738 B1 | * | 11/2004 | Johs et al. | 356/369 |
| 6,934,024 B2 | | 8/2005 | Zhan et al. | 356/369 |
| 7,061,561 B2 | | 6/2006 | Silverstein et al. | 349/117 |
| 7,083,835 B2 | | 8/2006 | Elman et al. | 428/1.3 |
| 7,136,162 B1 | | 11/2006 | Liphardt | 356/369 |
| 7,151,605 B1 | * | 12/2006 | Herzinger et al. | 356/369 |
| 7,163,724 B2 | | 1/2007 | Elman et al. | 428/1.3 |

(Continued)

OTHER PUBLICATIONS

Jellison Jr. G.E., Spectroscopic ellipsometry data analysis: Measured versus calculated quantities (1998) Thin Solid Films, 313-314, pp. 33-39.*

(Continued)

*Primary Examiner* — Mohsen Ahmadi  
*Assistant Examiner* — Shawn Decenzo  
(74) *Attorney, Agent, or Firm* — James D. Welch

(57) ABSTRACT

A method of applying spectroscopic ellipsometry to arrive at accurate values of optical and physical properties for thin films on samples having rough or textured surfaces.

14 Claims, 12 Drawing Sheets

U.S. PATENT DOCUMENTS

| | | | |
|---|---|---|---|
| 7,170,574 B2 | 1/2007 | Tan et al. | 349/117 |
| 7,209,234 B2 * | 4/2007 | Woollam et al. | 356/369 |
| 7,211,304 B2 | 5/2007 | Elman et al. | 428/1.3 |
| 7,221,420 B2 | 5/2007 | Silverstein et al. | 428/1.3 |
| 7,230,699 B1 * | 6/2007 | Liphardt et al. | 356/364 |
| 7,236,221 B2 | 6/2007 | Ishikawa et al. | 349/119 |
| 7,362,435 B1 * | 4/2008 | Johs et al. | 356/369 |
| 8,069,020 B2 * | 11/2011 | Li et al. | 703/6 |
| 2002/0024668 A1 | 2/2002 | Stehle et al. | |
| 2002/0091323 A1 | 7/2002 | Dreher | |
| 2003/0227623 A1 | 12/2003 | Zhan et al. | |
| 2004/0035529 A1 * | 2/2004 | Grimbergen | 156/345.24 |
| 2004/0152221 A1 * | 8/2004 | Engelhard et al. | 438/16 |
| 2004/0179158 A1 | 9/2004 | Silverstein et al. | |
| 2004/0189992 A9 | 9/2004 | Zhan et al. | |
| 2004/0208350 A1 | 10/2004 | Rea et al. | |
| 2005/0024561 A1 | 2/2005 | Elman et al. | |
| 2005/0128391 A1 | 6/2005 | Tan et al. | |
| 2005/0270458 A1 | 12/2005 | Ishikawa et al. | |
| 2005/0270459 A1 | 12/2005 | Elman et al. | |
| 2005/0286001 A1 | 12/2005 | Elman et al. | |
| 2006/0099135 A1 | 5/2006 | Yodh et al. | |
| 2006/0115640 A1 | 6/2006 | Yodh et al. | |
| 2006/0141466 A1 | 6/2006 | Pinet et al. | |
| 2006/0193975 A1 | 8/2006 | Elman et al. | |
| 2006/0203164 A1 | 9/2006 | Silverstein et al. | |
| 2006/0215158 A1 | 9/2006 | Saitoh | |
| 2009/0219537 A1 * | 9/2009 | Walsh | 356/445 |

OTHER PUBLICATIONS

Thomas A. Germer and Clara C. Asmail, "Polarization of light scattered by microrough surfaces and subsurface defects," J. Opt. Soc. Am. A 16, 1326-1332 (1999).*

Thomas A. Germer, "Polarized light scattering by microroughness and small defects in dielectric layers," J. Opt. Soc. Am. A 18, 1279-1288 (2001).*

PCT Publication WO 99/45340.

* cited by examiner

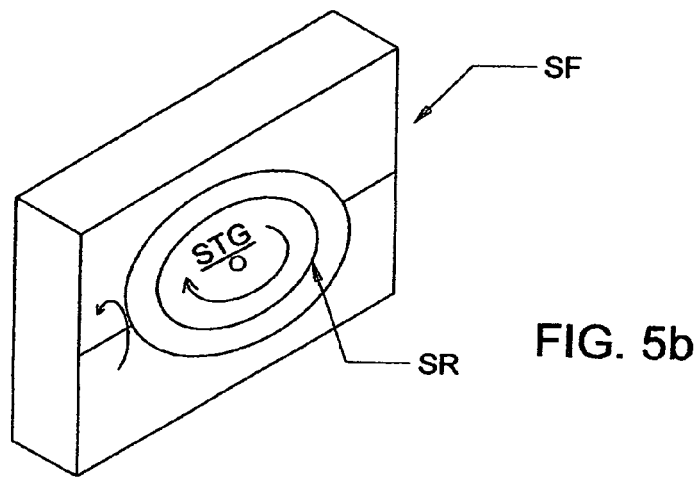
FIG. 5b
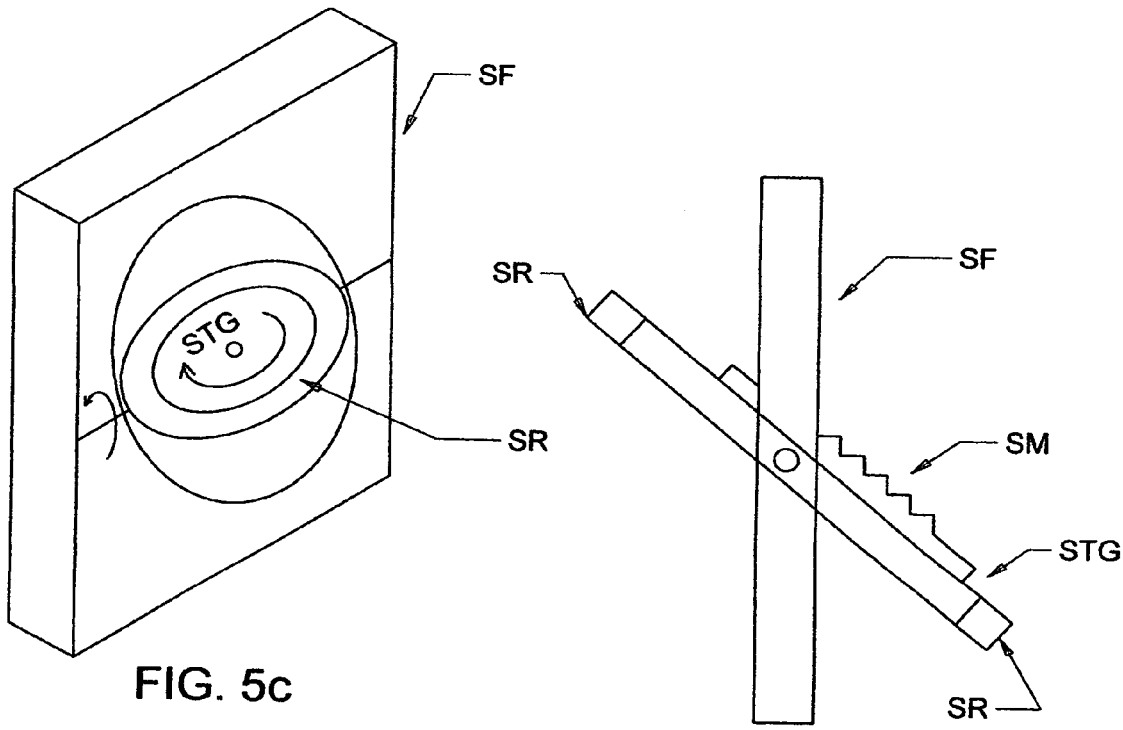
FIG. 5c
FIG. 5d

US 8,248,607 B1

EMPIRICAL CORRECTION FOR SPECTROSCOPIC ELLIPSOMETRIC MEASUREMENTS OF ROUGH OR TEXTURED SURFACES

CROSS-REFERENCE TO OTHER APPLICATIONS

This Application Claims Benefit of Provisional Application 61/273,372 Filed Aug. 4, 2009.

TECHNICAL FIELD

The present invention relates to investigation of samples having thin films present on a surface thereof, and more particularly is a method of applying beam scattering correction factors to arrive at accurate values for optical and physical properties of thin films on samples having rough or textured surfaces.

BACKGROUND

It is known to practice ellipsometry, polarimetry, reflectometry and spectophotometry to investigate samples with electromagnetic beams. Typically, samples investigated have a substantially smooth surface and the procedure involves taking data and regressing a mathematical model thereonto. Where a sample surface is not substantially smooth, however, but rather is rough or textured, it has been found that the typical approach leads to determination of values for physical and optical properties results which are not correct. While the data might appear qualitatively correct, it has been found that there is generally an offset between, for instance, values for the refractive index and extinction coefficient for a thin film on said rough or textured surface, as compared to values for the same thin film on a sample with a substantially smooth surface. This is because during measurements of rough or textured surfaces with spectroscopic electromagnetic radiation, much of the measurement beam can be scattered away from the detector. This significantly reduces the overall intensity reaching the ellipsometer detector. While it is true that Spectroscopic Ellipsometry (SE) measurements collect a ratio of light components and do not require the absolute intensity, the detected light can also be affected by the scattering or roughness. The effect of roughness on the data can be measured from an uncoated rough surface and then applied to coated rough surfaces to correct for the roughness effects on SE data. This is demonstrated to improve the accuracy of coating measurements on rough and textured surfaces.

As disclosed in Parent application Ser. No. 12/315,898, it is well known in the art to cause an electromagnetic beam to reflect from a sample, and by monitoring change in, for example, the intensity and/or polarization state of said beam resulting from interaction with the sample, determine properties of the sample, (eg. thickness of thin films on the sample surface, and optical constants). It is also known that where a sample surface reflects specularly essentially all incident electromagnetic radiation can be reflected from the sample into a detector and good data will typically be developed thereby. A problem can occur, however, where a sample has an irregular surface, as incident electromagnetic radiation becomes scattered by what amounts to the effects of said beam effectively approaching the sample surface at different angles and planes of incidence, at different locations thereon. When this occurs a large majority of the electromagnetic radiation which reflects from the sample surface is often directed other than into a detector, or is scattered, rather than specularly reflected thereinto, which scattered electromagnetic radiation causes problems in analysis of acquired data. The intensity of a collected portion of a reflected beam can then become too weak to be used in sample analysis and attempts to increase the intensity entering a detector, without consideration of from where on an irregular sample surface the additional collected electromagnetic radiation reflects, can lead to data which is noisy, depolarized, based on uncertain angles-of-incidence, and therefore can not be reliably analyzed to provide good results.

It is further known to place samples on stages in ellipsometer and the like systems, and to cause a polarized beam of electromagnetic radiation to impinge on said sample at an oblique angle thereto, interact with said sample and then enter a detector. It is also known that the "tilt" of a sample surface at a specific location thereon can affect realized angle and plane-of-incidence values actually achieved. Further, it is known to adjust the vertical height of the stage to position a sample such that a beam of electromagnetic radiation reflecting therefrom enters a detector. And, it is known to use a beam of electromagnetic radiation comprising a range of wavelengths, (eg. which can be smaller or larger than a facet feature on a sample to enable), investigation thereof).

Continuing, as it is relevant, Patent to Abraham et al., U.S. Pat. No. 6,091,499 is disclosed as it describes a method and system for automatic relative adjustment of samples in relation to an ellipsometer. Paraphrasing, said Abraham et al. system basically comprises:

a system for orienting a sample on a stage in an ellipsometer system comprising a first light source, a polarizer, said stage, an analyzer and a detector;

said system further comprising a detection system having a second light source, wherein said detection system is independently adjustable in relation to said ellipsometer, and wherein said detection system can be electronically locked into position relative to said ellipsometer so that said ellipsometer and said detection system can be adjusted as one unit in relationship to said stage, wherein said detection system can detect both a tilt of a sample placed onto said stage, and a distance of said sample from a coordinate source of the ellipsometer in two perpendicular axes; and said system further comprising an adjusting device, wherein said adjusting device can adjust tilt of said stage, and wherein said adjusting device can adjust the position of said ellipsometer and detection system when in an electronically locked relationship with respect to one another.

The 499 Patent drawings show a single source, (identified as (21)), provides, via beam splitters and reflection means, normal and oblique angle-of-incidence electromagnetic beams to a sample, which normal and oblique angle-of-incidence electromagnetic beams are each intercepted by a different detector, (identified as (24) and (25) respectively), after reflecting from the sample. The associated ellipsometer system comprises a separate source, (identified as (11)).

Additional known related Patents are:
Patent to Coates U.S. Pat. No. 4,373,817;
Patent to Coates U.S. Pat. No. 5,045,704;
RE. 34,783 to Coates;
Patent to Mikkelsen et al., U.S. Pat. No. 6,600,560;
Patent to Fanton et al., U.S. Pat. No. 5,596,411;
Patent to Piwonka-Corle et al., U.S. Pat. No. 5,910,842;
Patent to Piwonka-Corle et al., U.S. Pat. No. 5,608,526;
Patent to Bareket, U.S. Pat. No. 5,889,593;
Patent to Norton et al., U.S. Pat. No. 5,486,701;
Patent to Aspnes et al., U.S. Pat. No. 5,900,939;

Patent to Aspnes et al., U.S. Pat. No. 5,798,837;
Patent to Rosenscwaig et al., U.S. Pat. No. 5,412,473;
Patent to Carter et al., U.S. Pat. No. 5,771,094;
Patent to Liphardt, U.S. Pat. No. 7,136,162;
PCT Application Publication WO 99/45340;
Published Application of Stehle et al., No. US2002/0024668 A1.

Additionally, a recent computer search using the words "solar cell" and "sample tilt" provided no hits, while using the words "solar cell" and "substrate tilt" provided one hit each for Patents and Published Applications, (eg. U.S. Pat. No. 5,388,635 and Published Application US 2007/0267711), and using the words "solar cell" and "stage tilt" provided two hits each for Published Applications, (eg. US 2006/0048800 and 2004/0056779). None of these identified references are considered relevant.

Provisional Application Ser. No. 61/126,233 filed May 2, 2008 in incorporated herein by reference.

As the system of the present invention includes intensity controlling "crossed-polarizers", U.S. Patents and Published Applications were identified which include the terms "crossed-polarizer" and "ellipsometry" or "ellipsometer", and are:

Patents
U.S. Pat. Nos. 7,236,221; 7,221,420; 7,211,304; 7,163,724; 7,083,835; 7,061,561; 6,934,024; 6,798,511; 6,693,711; 6,112,114; 5,787,890; 5,303,709; 4,097,110; 7,170,574;
Published Applications
2006/0215158; 2006/0203164; 2006/0193975; 2005/0286001; 2005/0270459; 2005/0270458; 2005/0024561; 2004/0189992; 2004/0179158; 2003/0227623; 2003/0227623; 2002/0091323; 2006/0141466; 2006/0115640; 2006/0099135; 2005/0270458; 2005/0128391; 2004/0208350; 2004/0189992; 2003/0227623; 2002/0091323.

A USPTO data base computer search of both Patents and Published Applications using "scatter matrix" and "ellipsometer" or "ellipsometry" did not produce any hits. Where "correction matrix" is substituted a Patent to Jellison Jr. et al. No. 5,956,147 was identified, but no Published Applications were found. The 147 Patent concerns calibration of a two modulator generalized ellipsometer, however, and not to investigation of rough or textured samples.

Finally, while there is no known published disclosure thereof, Applicants have heard, "through the grapevine", that another entity (ie. Sentech), is using a large sample tilt technique similar to that disclosed herein, to facilitate investigation of solar cells. However, Applicants believe this alternative use is of very recent implementation and, for instance, does not involve use of spectroscopic electromagnetic radiation nor involve application of a sample stage rotation. Said usage is not known to involve the correction mechanism which is the focus of the present invention.

An approach to investigating a sample with a "regularly" textured surface, (ie. it comprises a surface having a repeated faceted pattern thereupon) and/or a surface characterized by an irregular array of faceted structures, would provide utility. If possible, such an approach would allow a researcher to collect an increased amount of "information containing" electromagnetic radiation which reflects from said sample textured surface and enters a detector to produce good data. This is especially the case where a correction approach allows arriving at values for thin film characteristics determined on rough or textured surfaces which match those determined from samples with smooth surfaces. It is such an approach that is subject of the present invention.

The present invention provides an approach to coordinating results obtained from investigation of a thin film present on a sample with a rough or textured sample to results obtained from investigating of a thin film present on a sample with a substantially smooth surface.

DISCLOSURE OF THE INVENTION

To being, while the disclosure herein beneficially uses the rough or textured surface of solar cells as an example, it is to be understood that this is not a limitation. The present methodology can be used to improve results when any rough or textured surface is investigated.

Continuing, for insight it is noted that application Ser. No. 12/315,898 discloses that, while the invention therein is very much related to sample orientation aspects, it was understood that said Application is primarily focused on aligning a sample to assure the Angle-of-Incidence (AOI) and Plane-of-Incidence (POI) of a beam of electromagnetic radiation which impinges on a specific identified location (a focused beam can be used), on a sample are known with precision so as to enable better analysis of data. That is, prior art Applications and Patents are focused primarily on an approach to aligning a sample via a tip/tilt action of a stage that supports the sample in a plane, optionally in combination with adjusting the position of the stage along a normal to said plane for each position on a sample which is investigated. Provision for rotating the stage about a normal thereto is also disclosed in said prior art Applications and Patents. Said approach is sequentially applied to samples with irregular surfaces at different locations thereupon. The 898 Application invention also involves adjusting the tip/tilt of a stage that supports the sample in a plane, but the focus thereof is modified to introducing a very significant stage tilt, (eg. demonstrated by FIG. 5$d$ herein which shows a FIG. 5$a$ stage (STG), optionally in combination with a Sample Rotation (SR) means, so that surface facets which are repeated in a textured sample surface (eg. see FIG. 3b in U.S. Pat. No. 7,230,699 and equivalent, FIG. 3$c$ herein), are oriented to reflect electromagnetic radiation incident thereupon over a more significant area thereof, (eg. compare FIGS. 3$b$ and 4$a$ herein, with said FIG. 4$a$ showing the preferred orientation), into a detector, while electromagnetic radiation incident on other locations of the textured sample are scattered away from the detector, (eg. see FIG. 3$a$ herein). Where sample facet dimensions are less equal in orthogonal directions, (eg. see FIG. 4$c$ herein), the 699 Patent FIG. 3b, (FIG. 3$c$ herein), orientation capability can be used without rotation about a normal to the Stage (STG) Surface.

It is noted that typically, the incident beam of electromagnetic radiation used in practicing the 898 Application invention is not focused and its diameter is very large (eg. orders of magnitude larger), compared to facet dimensions of surfaces which are repeated in a textured sample surface and which are to be oriented to reflect electromagnetic radiation incident thereupon into a detector. Further, the 898 Application invention can provide for collecting electromagnetic radiation reflected from the facets on the sample and focusing it into a detector.

For clarity, it is directly stated that the 898 Application invention retains its Parent Application's and Patent's focus of aligning a sample to assure the Angle-of-Incidence (AOI) and Plane-of-Incidence (POI) of a beam of electromagnetic radiation which impinges on a specific identified location, (a focused beam can be used), on a sample are known with precision so as to enable better analysis of data, but further introduces use of a significant sample tilt to orient sample facets as described above. That is, the 898 Application invention provides that the (AOI) and (POI) are accurately known at many locations on a textured sample, simultaneously.

It is mentioned that another approach to increasing the intensity of electromagnetic radiation reflected from a "rough" surface is to direct the beam to impinge on the rough surface at a large oblique AOI. This will result in an increased intensity entering a detector positioned to intercept the reflected beam, but a problem remains in that the data provided thereby typically contains so much noise, depolarized components and the like, that it can not be beneficially analyzed. While use of a very high AOI is within the scope of the 898 Application invention, the 898 Application invention teaches combining that with use of a very high tilt angle (again see FIG. 5d with reference to FIGS. 5a and 5b herein for Stage (STG) orientation capability). It is also disclosed that the optimum Stage Tilt angle is not necessarily what is computed from a known crystalline structure facet angle. For instance, (111) Silicon can be etched to provide facets which have an associated angle of 51.7 degrees. FIG. 4c herein provides insight to such a sample. It has been found in experimentation that an optimum stage calculated Tilt, (see FIG. 5d), for providing the greatest amount of reflected electromagnetic radiation into a detector is not necessarily that which exactly compensates this angle. In fact, the preferred embodiment of the 898 Application invention methodology provides for use of other than an optimum calculated Tilt.

Continuing, in view of the foregoing, it should be appreciated that where a surface of a sample has a non-random textured surface with some faceted regularly repeated pattern, it is possible to collect an increased amount of "information containing" electromagnetic radiation which reflects from said sample surface and enters a detector, by optimizing the orientation of the sample surface texturing. Such a sample can be characterized as having the presence of a plurality of surface facet regions in planes which are substantially parallel to one another which can be simultaneously oriented. This is basically no different from the approach taught in Parent U.S. Pat. No. 7,230,699, except that in the 898 Application invention an electromagnetic beam diameter is intentionally significantly larger than facets being investigated so that many facets simultaneously reflect electromagnetic radiation into a detector.

The 898 Application invention comprises a method of analyzing physical and optical properties of a textured sample surface comprises:
 a) providing an ellipsometer or the like system comprising:
  a source of a spectroscopic beam of electromagnetic radiation;
  a polarizer;
  a stage system comprising:
   a stage frame oriented in a stage frame plane, and a stage; said stage being rotatably connected to said stage frame in a manner enabling tilting said stage with respect to said stage frame plane;
  an analyzer; and
  a detector.
Said spectroscopic ellipsometer can optionally further comprise at least one selection from the group consisting of:
 a means for controlling beam intensity between the source and detector;
 a variable attenuator for controlling beam intensity between the source and detector;
 a variable attenuator comprising two polarizers which can be adjusted with respect to one another to control the amount of electromagnetic radiation passing therethrough, between the source and detector;
 a sequence of filters for controlling beam intensity between the source and detector; and
 said source of a spectroscopic beam of electromagnetic radiation is a plurality of sources for providing a plurality of beam intensities;
or the like.
Said method continues with the following steps:
 b) positioning a textured sample onto said stage;
 c) causing a spectroscopic beam of electromagnetic radiation, provided by said source thereof, to pass through said polarizer, impinge on and reflect from said textured sample surface, pass through said analyzer and enter said detector;
 d) effecting a stage tilt to orient said textured sample surface in a plane oriented at between 10-90 degrees with respect to the plane of said stage frame;
 e) collecting data provided by said detector; and
 f) analyzing collected detector data to determine physical and/or optical properties of said textured sample surface.
The 898 Application can include the step:
 g) performing at least one selection from the group consisting of:
  storing at least some data provided by said data detector in machine readable media;
  analyzing at least some of the data provided by said data detector and storing at least some of the results of said analysis in machine readable media;
  displaying at least some data provided by said data detector by electronic and/or non-electronic means;
  analyzing at least some of the data provided by said data detector and displaying at least some of the results of said analysis by electronic and/or non-electronic means;
  causing at least some data provided by said data detector to produce a signal which is applied to provide a concrete and tangible result; and
  analyzing at least some of the data provided by said data detector and causing at least some thereof to produce a signal which is applied to provide a concrete and tangible result.
Note, the range of 10-90 degrees is typical, but rotation can be effected between 0-90 degrees. Further, said range is to be interpreted to include 0 to negative (−90) degrees.

It is noted that at the location on said textured sample at which said spectroscopic beam of electromagnetic radiation impinges thereupon, there is identified a perpendicular to said surface,
 in which a plane-of-incidence is defined as that plane including both said spectroscopic beam locus and said perpendicular to said textured surface at said location whereat said beam impinges; and
 in which an angle-of-incidence is defined as that angle between the locus of said spectroscopic beam and said normal to said textured surface at said location whereat said beam impinges;
and said method can further comprise the step of causing the sample to tilt so that said perpendicular to said textured sample surface is not in said defined plane-of-incidence while data is collected in step e.

Said method can involve the sample tilt being set to a value at which quality of said reflected beam reaching said detector is substantially optimized.

Said method can involve the angle-of-incidence at which said spectroscopic beam approaches said textured sample being set to a value at which quality of said reflected spectroscopic beam reaching said detector is substantially optimized.

Said method can be characterized by at least one selection from the group consisting of:

a) a thin film is present on the surface of the textured sample which is in a tilted plane oriented at between 10-80 degrees with respect to the plane of said stage frame;

b) the surface of the textured sample is oriented in a tilted plane oriented at an angle with respect to the plane of said stage frame which is other than what the angle of facets on the textured sample would indicate as optimum;

c) the angle-of-incidence at which the beam of electromagnetic radiation impinges on said thin film on said textured sample surface is between 10 and 80 degrees, and surface of the textured sample is in a tilted plane oriented at between 10-90 degrees with respect to the plane of said stage frame;

d) the surface of the textured sample is in a tilted plane oriented at between 0-90 degrees with respect to the plane of said stage frame and said textured sample is rotated about a normal to said tilted plane to optimize a signal which enters said detector, and said beam of electromagnetic radiation is spectroscopic;

e) said ellipsometer further comprises a means for increasing the intensity of the beam of electromagnetic radiation which impinges on and reflects from said surface of said textured sample surface;

f) said surface of said textured sample comprises facets from which electromagnetic radiation incident thereupon is reflected along loci other than into said detector;

g) said surface of said textured samples comprise a non-random effectively "regular" textured surface and/or a surface characterized by an irregular array of faceted structures;

h) said surface of said textured sample comprises connector lines thereupon from which electromagnetic radiation incident thereupon is reflected along loci other than into said detector;

i) said ellipsometer further comprises "X"-"Y" or R-THETA means for translating said stage and stage rotation means as a unit.

Another 898 Application method of analyzing physical and optical properties of a textured sample surface comprises:

a) providing an ellipsometer or the like system comprising:
a source of a beam of electromagnetic radiation;
a polarizer;
a stage system comprising:
a stage frame oriented in a stage frame plane;
a stage rotation means; and
a stage;
said stage rotation means being rotatably connected to said stage frame in a manner enabling tilting said stage and stage rotation means, as a unit, with respect to said stage frame plane and said stage rotation means enabling rotation of said stage in a plane parallel to
the surface of said stage;
an analyzer; and
a detector.

Said spectroscopic ellipsometer can optionally further comprise at least one selection from the group consisting of:

a means for controlling beam intensity between the source and detector;

a variable attenuator for controlling beam intensity between the source and detector;

a variable attenuator comprising two polarizers which can be adjusted with respect to one another to control the amount of electromagnetic radiation passing therethrough, between the source and detector;

a sequence of filters for controlling beam intensity between the source and detector; and said source of a spectroscopic beam of electromagnetic radiation is a plurality of sources for providing a plurality of beam intensities;

or the like.

Said method continues with the steps:

b) positioning a textured sample onto said stage;

c) causing a beam of electromagnetic radiation, provided by said source thereof, to pass through said polarizer, impinge on and reflect from said textured sample surface, pass through said analyzer and enter said detector;

d) effecting a stage tilt to orient said textured sample surface in a plane oriented at between 10-90 degrees with respect to the plane of said stage frame;

e) collecting data provided by said detector; and f) analyzing collected detector data to determine physical and/or optical properties of said textured sample surface.

In addition said method can include:

g) performing at least one selection from the group consisting of:

storing at least some data provided by said data detector in machine readable media;

analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result; and analyzing at least some of the data provided by said data detector and causing at least some thereof to produce a signal which is applied to provide a concrete and tangible result.

It is again noted that at the location on said textured sample at which said beam of electromagnetic radiation impinges thereupon, there is identified a perpendicular to said surface, in which a plane-of-incidence is defined as that plane including both said beam locus and said perpendicular to said textured surface at said location whereat said beam impinges; and in which an angle-of-incidence is defined as that angle between the locus of said beam and said normal to said textured surface at said location whereat said beam impinges;

and said method can further comprise the step of causing the sample to tilt so that said perpendicular to said textured sample surface is not in said defined plane-of-incidence while data is collected in step e.

Said method can involve the sample tilt being set to a value at which quality of said reflected beam reaching said detector is substantially optimized.

Said method can involve the angle-of-incidence at which said beam approaches said textured sample being set to a value at which quality of said reflected beam reaching said detector is substantially optimized.

Said method can involve the stage rotation means being applied to cause said stage to rotate in a plane substantially parallel to said textured sample surface to a position at which quality of said reflected beam reaching said detector is substantially optimized.

Said method can involve, in the step a) providing an ellipsometer or the like system which further comprises providing a means for controlling the intensity of the spectroscopic beam per se. that enters the detector. Though not limiting, said means for controlling the intensity of the spectroscopic beam per se. can comprise a selection from the group consisting of:
> rotatable crossed polarizers placed into said beam;
>> a series of different opaque filters which can be sequentially inserted into said beam;
>> a series of different intensity sources.

While not a primary focus of the 898 Application, it is mentioned that, as disclosed in Application Serial No. 12/075,956, the rotatable crossed polarizer approach can control beam intensity as a function of wavelength, where a source thereof provides a polychromatic beam. A sequence of crossed polarizers can involve the second thereof being a beam polarizer in an ellipsometer or polarimeter system, which provides a set beam polarization state to a substrate. When the first of said crossed polarizers is rotated with respect thereto, the intensity exiting the second thereof is, substantially uniformly, controlled over the entire range of wavelengths. The crossed polarizer system can, however, further comprise a compensator placed in between the first and second of the crossed polarizers, and said compensator serves to provide selective attenuation of some wavelengths more than others. It is to be understood that the compensator just mentioned is not that involved in configuring a rotation compensator ellipsometer system. In a rotation compensator ellipsometer system an additional compensator is placed between the second crossed polarizer and an analyzer which is positioned before a detector, and it is that additional compensator which is caused to rotate during data acquisition. This is not to be considered, however, as limiting application of the 898 Application invention to being implemented with only rotating compensator systems. It is specifically disclosed that the 898 Application invention can be practiced using any type of ellipsometer or polarimeter system. In particular, this includes rotating polarizer, rotation analyzer and phase modulation systems. Further, where a compensator is applied it can be of Berek-type, where the optical axis is perpendicular to a surface thereof into which a beam is entered, and where a "tipping" of said Berek-type compensator is used to affect a phase angle between orthogonal components of a polarized beam passed therethrough, or it can be of a conventional-type where the optical axis is parallel to a surface thereof into which a beam is entered, and where a "rotation" of said conventional-type compensator is used to affect a phase angle between orthogonal components of a polarized beam passed therethrough.

Said method can involve an ellipsometer/sample combination characterized by at least one selection from the group:
> a) a thin film is present on the surface of the textured sample which is in a tilted plane oriented at between 10-80 degrees with respect to the plane of said stage frame;
> b) the surface of the textured sample is oriented in a tilted plane oriented at an angle with respect to the plane of said stage frame which is other than what the angle of facets on the textured sample would indicate as optimum;
> c) the angle-of-incidence at which the beam of electromagnetic radiation impinges on said thin film on said textured sample surface is between 10 and 80 degrees, and surface of the textured sample is in a tilted plane oriented at between 10-90 degrees with respect to the plane of said stage frame;
> d) the surface of the textured sample is in a tilted plane oriented at between 0-90 degrees with respect to the plane of said stage frame and said textured sample is rotated about a normal to said tilted plane to optimize a signal which enters said detector, and said beam of electromagnetic radiation is spectroscopic;
> e) said ellipsometer further comprises a means for increasing the intensity of the beam of electromagnetic radiation which impinges on and reflects from said surface of said textured sample surface;
> f) said surface of said textured sample comprises facets from which electromagnetic radiation incident thereupon is reflected along loci other than into said detector;
> g) said surface of said textured samples comprise a non-random effectively "regular" textured surface and/or a surface characterized by an irregular array of faceted structures;
> h) said surface of said textured sample comprises connector lines thereupon from which electromagnetic radiation incident thereupon is reflected along loci other than into said detector;
> i) said ellipsometer further comprises "X"-"Y" or R-THETA means for translating said stage and stage rotation means as a unit.

The 898 Application invention can be practiced using a spectroscopic ellipsometer which comprises:
> a spectroscopic source of a beam of electromagnetic radiation;
> a polarizer;
> a stage system comprising:
>> a stage frame oriented in a stage frame plane;
>> a stage rotation means; and
>> a stage;
>> said stage rotation means being rotatably connected to said stage frame in a manner enabling tilting said stage and stage rotation means, as a unit, with respect to said stage frame plane and said stage rotation means enabling rotation of said stage in a plane parallel to the surface of said stage;
> an analyzer; and
> a detector.

Said spectroscopic ellipsometer can optionally further comprise at least one selection from the group consisting of:
> a means for controlling beam intensity between the source and detector;
> a variable attenuator for controlling beam intensity between the source and detector;
> a variable attenuator comprising two polarizers which can be adjusted with respect to one another to control the amount of electromagnetic radiation passing therethrough, between the source and detector;
> a sequence of filters for controlling beam intensity between the source and detector; and
> said source of a spectroscopic beam of electromagnetic radiation is a plurality of sources for providing a plurality of beam intensities;

or the like.

Said system can further comprise at least one compensator between the polarizer and analyzer positioned so that the beam of electromagnetic radiation provided by said spectroscopic source of a beam of electromagnetic radiation, which interacts with said textured sample, passes therethrough, and causing said at least one compensator to rotate substantially about the locus of said beam of electromagnetic radiation during the step of obtaining ellipsometric data over a spectroscopic range of wavelengths.

Another 898 Application invention method of improving results achieved by investigating a sample with a textured surface with electromagnetic radiation comprises:
> a) providing a spectroscopic ellipsometer as described above;
> b) placing a sample with a specularly reflecting surface on said stage;

c) while causing said a spectroscopic source of a beam of electromagnetic radiation to direct a spectroscopic beam of electromagnetic radiation to pass through said a variable attenuator and polarizer, toward said specular surface of said sample with a specularly reflecting surface, in coordination, adjusting the angle-of-incidence of said spectroscopic beam of electromagnetic radiation with respect to said sample, and the orientation of said sample by adjustment of said stage rotation means adjusting the orientation of said stage and stage rotation means, as a unit, with respect to said stage frame plane, and optionally adjusting said stage rotation to orient the surface of said sample a plane parallel to the surface of said stage, so that the electromagnetic radiation reflected from said sample passes through said analyzer and enters said detector;

d) adjusting said variable attenuator so that the intensity of the reflected electromagnetic radiation entering said detector does not saturate said detector;

e) removing said sample with a specular surface from said stage and placing a sample with a textured surface thereupon in its place;

f) in coordination adjusting the variable attenuator, and the orientation of said textured sample surface by adjustment of said stage rotation means, and tilting said stage and stage rotation means as a unit, with respect to said stage frame plane so that the electromagnetic radiation reflected from said sample with a textured surface passes through said analyzer and enters said detector;

g) obtaining ellipsometric data over a spectroscopic range of wavelengths;

h) analyzing said ellipsometric data to evaluate optical and physical properties of said textured sample.

Said method can further include providing at least one compensator between the polarizer and analyzer positioned so that the beam of electromagnetic radiation provided by said spectroscopic source of a beam of electromagnetic radiation, which interacts with said textured sample, passes therethrough, and causing said at least one compensator to rotate substantially about the locus of said beam of electromagnetic radiation during the step of obtaining ellipsometric data over a spectroscopic range of wavelengths. In the alternative said polarizer and/or analyzer can caused to rotate during data acquisition.

Said method can involve investigating a sample with a textured surface characterized by the presence of a plurality of facet surfaces which are substantially parallel to one another, and the step of adjusting said stage rotation means, and titling said stage and stage rotation means as a unit, with respect to said stage frame plane, so that the electromagnetic radiation reflected from said sample with a textured surface passes through said analyzer and enters said detector involves effecting orientation of said sample so that electromagnetic radiation reflecting from said plurality of facet surfaces which are substantially parallel to one another enters said detector, which substantially all electromagnetic radiation which does not reflect from said plurality of facet surfaces which are substantially parallel to one another does not so enter said detector. The preferred system for providing this capability is better discussed later in this Section of this Specification.

Said method can involve investigation of the textured surface of said sample is coated with a thin film, and the steps of obtaining ellipsometric data over a spectroscopic range of wavelengths and analyzing said ellipsometric data to evaluate physical and optical properties of said textured sample can involve determining physical and optical properties of said thin film. For instance, an 898 Application invention method can involve analyzing physical and optical properties of a thin film on a textured sample front side surface, where said sample has a similarly textured backside without the thin film being present thereupon, or a region on the front side that has no thin film present, or a different but essentially similar sample that has a region without a thin film present thereupon can even be applied. As alluded to before, said sample texturing is characterized as a non-random effectively "regular" textured surface and/or a surface characterized by an irregular array of faceted structures. Said method comprises the steps of:

a) obtaining ellipsometric data for both said sample with, and without a thin film present, (eg. from both the front and back sides of said sample by taking data from one side and then flipping the sample over and again acquiring data, or from regions comprising and not comprising a thin film on the one side thereof or by obtaining data from different but essentially similar samples which in combination provide both film present and absent regions);

b) proposing a mathematical/optical model for the sample without a thin film present, and a mathematical/optical model for the sample front side which has a thin film present;

c) fitting said ellipsometric data obtained from the sample without a thin film present to said mathematical/optical model for said sample without a thin film present to obtain values for sample per se. physical and optical properties, such as effective media surface roughness and/or void percentage;

d) while holding values for the sample per se. physical and optical properties determined in step c, fitting said ellipsometric data obtained from the side of said sample having a thin film present to said mathematical/optical model for said side having a thin film present to obtain values for said thin film physical and optical properties.

Another method of analyzing physical and optical properties of a thin film on a textured sample front side surface comprises:

a) providing an ellipsometer or the like system comprising:
  a source of a beam of electromagnetic radiation;
  a polarizer;
  a stage system comprising:
    a stage frame oriented in a stage frame plane;
    a stage rotation means; and
    a stage;
    said stage rotation means being rotatably connected to said stage frame in a manner enabling tilting said stage and stage rotation means, as a unit, with respect to said stage frame plane and said stage rotation means enabling rotation of said stage in a plane parallel to the surface of said stage;
  an analyzer; and
  a detector.

Said spectroscopic ellipsometer can optionally further comprise at least one selection from the group consisting of:
  a means for controlling beam intensity between the source and detector;
  a variable attenuator for controlling beam intensity between the source and detector;
  a variable attenuator comprising two polarizers which can be adjusted with respect to one another to control the amount of electromagnetic radiation passing therethrough, between the source and detector;
  a sequence of filters for controlling beam intensity between the source and detector; and said source of a spectroscopic beam of electromagnetic radiation is a plurality of sources for providing a plurality of beam intensities.

Said method then further comprises:
- b) positioning a textured sample onto said stage with the thin film on surface of said textured sample facing away therefrom;
- c) causing a beam of electromagnetic radiation, provided by said source of a beam of electromagnetic radiation, to pass through said polarizer, impinge on and reflect from said textured sample, pass through said analyzer and enter said detector;
- d) effecting a stage and stage rotation means tilt to orient said textured sample surface having a thin film thereupon in a plane oriented at, for instance, between 10-80 degrees with respect to the plane of said stage frame;
- e) while monitoring detector data output, causing said stage rotation means to rotate the textured sample in the plane parallel to the surface of said stage until said data output is of a sufficient quality to allow beneficial analysis thereof;
- f) repeating steps d and e using different stage and stage rotation means tilt to orient said textured sample surface having a thin film thereupon in a different plane oriented at between, for instance, 10-80 degrees with respect to the plane of said stage frame, until a best combination of stage and stage rotation means tilt, and stage rotation in the plane parallel to the surface of said stage is determined based on data output being of a sufficient quality to allow beneficial analysis thereof;
- g) analyzing detector data collected to determine physical and/or optical properties of said thin film on said textured sample front side surface.

Said method can further comprise placing said textured sample onto said stage with the thin film on surface of said textured sample facing theretoward and causing a beam of electromagnetic radiation, provided by said source of a beam of electromagnetic radiation, to pass through said polarizer, impinge on and reflect from said backside of said textured sample, pass through said analyzer and enter said detector, followed by analyzing data provided by said detector to evaluate parameters corresponding to the non-thin film substrate component of said textured sample, and using the results in the procedure to better evaluate the physical and optical properties of the thin film. As mentioned above, a region on the sample front side that has no thin film present, or a different but essentially similar sample that has a region without a thin film present thereupon can even be applied instead of data acquired by investigating the back side.

The foregoing method can also be characterized by at least one selection from the group consisting of:
- a) the thin film on the surface of the textured sample is in a tilted plane oriented at, for instance, between 10-80 degrees with respect to the plane of said stage frame, and said beam of electromagnetic radiation is spectroscopic;
- b) the thin film on the surface of the textured sample is oriented in a tilted plane oriented at an angle with respect to the plane of said stage frame which is other than what the angle of facets on the textured sample would indicate as optimum, and said beam of electromagnetic radiation is spectroscopic;
- c) the angle-of-incidence at which the beam of electromagnetic radiation impinges on said thin film on said textured sample surface is between 10 and 80 degrees, and the thin film on the surface of the textured sample is in a tilted plane oriented at between 10-90 degrees with respect to the plane of said stage frame, and said beam of electromagnetic radiation is spectroscopic;
- d) the thin film on the surface of the textured sample is in a tilted plane oriented at between 0-90 degrees with respect to the plane of said stage frame and said textured sample is rotated about a normal to said tilted plane to optimize a signal which enters said detector, and said beam of electromagnetic radiation is spectroscopic;
- e) said ellipsometer further comprises a means for increasing the intensity of the beam of electromagnetic radiation which impinges on and reflects from said surface of said textured sample surface;
- f) said surface of said textured sample comprises facets from which electromagnetic radiation incident thereupon is reflected along loci other than into said detector;
- g) said surface of said textured samples comprise a non-random effectively "regular" textured surface, and/or a surface characterized by an irregular array of faceted structures;
- h) said surface of said textured sample comprises connector lines thereupon from which electromagnetic radiation incident thereupon is reflected along loci other than into said detector;
- i) said ellipsometer further comprises "X"-"Y" or R-THETA means for translating said stage and stage rotation means as a unit.

As regards h) above, for clarity it is further noted that where the surface of said textured sample comprises connector lines thereupon, (eg. current collecting traces on a solar cell), they do not lie in the same plane as do, for instance, facet surfaces. It should be apparent that if the sample is tilted so that electromagnetic radiation incident thereupon reflects into a detector from facet surfaces, then electromagnetic radiation which reflects from the connector lines will reflect along loci in a plane other than appropriate to direct it into said detector.

In the foregoing method, it is also disclosed that it is further possible to simultaneously analyze data obtained at a plurality of stage tip, tilt and rotation settings.

It is noted that any of the methods disclosed herein can further include performing at least one selection from the group consisting of:
- storing at least some data provided by said data detector in machine readable media;
- analyzing at least some of the data provided by said data detector and storing at least some of the results of said analysis in machine readable media;
- displaying at least some data provided by said data detector by electronic and/or non-electronic means;
- analyzing at least some of the data provided by said data detector and displaying at least some of the results of said analysis by electronic and/or non-electronic means;
- causing at least some data provided by said data detector to produce a signal which is applied to provide a concrete and tangible result; and
- analyzing at least some of the data provided by said data detector and causing at least some thereof to produce a signal which is applied to provide a concrete and tangible result.

For additional insight, as an important capability of the Present Invention System is control of beam intensity, the preferred 898 Application invention system adds a control polarizer, and optionally a sequentially located control compensator, between the source of a beam of electromagnetic radiation and the beam polarizer in ellipsometer or polarimeter system, such that a beam of electromagnetic radiation provided by the source thereof passes through the control polarizer and optionally, when present, the control compensator, then through the beam polarizer and impinge on a sample, interact therewith, (eg. typically reflect therefrom but possibly transmit therethrough), and then pass through the analyzer and into the detector. Again, the control polarizer is positioned before the beam polarizer and in use is rotated with respect to the beam polarizer to substantially uniformly attenuate the intensity of all wavelengths which pass through said beam polarizer. And again, the 898 Application invention can also position a control compensator between the control and beam polarizers, which control compensator can be applied to cause selective attenuation of some wavelengths in the spectrum more than others. In use the beam polarizer is caused to set a polarization state in a beam exiting therefrom, and the control polarizer is rotated with respect to said beam polarizer to substantially uniformly control the intensity of the beam exiting the beam polarizer over a spectrum of wavelengths. The system can further comprise adjustment of a compensator between said control and beam polarizers which serves to cause selective attenuation of some wavelengths more than others in said spectrum of wavelengths. (It is noted that where a Berek-type control compensator, which has its optical axis perpendicular to a surface thereof which a beam enters is used, the terminology "rotation" thereof should be interpreted to mean a tipping thereof to position the optical axis other than parallel to the locus of the beam which passes therethrough, and where the control compensator has its optical axis in the plane of a surface thereof which a beam enters is used, rotation should be interpreted to means an actual rotation about a perpendicular to said surface).

A method of controlling the intensity of a beam of electromagnetic radiation over a spectral range, comprises the steps of:

a) providing a system for controlling the intensity of a beam of electromagnetic radiation as described above;

b) setting a beam polarization state with the beam polarizer and rotating the control polarizer with respect thereto to control the intensity.

Said method can further comprise providing a compensator between said control and beam polarizers which serves to selectively attenuate the intensity of some wavelengths in said spectrum more than others.

A typical procedure provides that the control and beam polarizers be rotated with respect to one another so that less intensity than is possible from the source, proceeds to the sample. This might be approached using a highly reflective test sample, for instance and the control polarizer adjusted to provide a non-saturating signal to the detector. When a less reflective sample is investigated, the control and beam polarizers can then be rotated with respect to one another so that greater intensity is applied to the less reflective sample. When present, the control compensator can be also be adjusted to further control the intensity vs. wavelength characteristic of a beam impinging on the sample.

For clarity, it is recited that the 898 Application invention can comprise an ellipsometer or polarimeter system comprising means for controlling the intensity of a beam of electromagnetic radiation as a function of wavelength comprising:

a source of a polychromatic beam of electromagnetic radiation;

a sequence of a control polarizer, a control compensator and beam polarizer;

said control and beam polarizers and said control compensator being rotatable with respect to one another, said system further comprising:

an analyzer; and a detector;

such that in use the polarized beam provided by said source which exits said beam polarizer, interacts with a sample and then passes through said analyzer and into said detector;

such that in use the beam polarizer is caused to set a polarization state in a beam exiting therefrom, and the control polarizer and control compensator can be rotated with respect to said beam polarizer to substantially uniformly control the intensity of the beam exiting the beam polarizer over a spectrum of wavelengths.

Said ellipsometer or polarimeter system can further comprise at least one system compensator between said beam polarizer and said analyzer.

The 898 Application invention also comprises a method of controlling the intensity of a beam of electromagnetic radiation over a spectral range, comprising the steps of:

a) providing an ellipsometer or polarimeter system as described just above;

b) setting a beam polarization state with the beam polarizer and rotating the control polarizer and/or control compensator with respect thereto to control the intensity of said beam over the spectrum of wavelengths.

PRESENT INVENTION

In practice of the disclosed 898 Application methodology, it has been discovered that, for instance, ellipsometric PSI and DELTA values produced for thin films on rough or textured surfaces are not what one finds when practicing the same methodology on for the same thin film on a smooth surface. The reason is that electromagnetic radiation in the rp and rs components are variously scattered, thereby changing the rp/rs ratio.

Turning now to the focus of the present invention, where it is desired to coordinate results obtained from investigation of a thin film present on a sample with a rough or textured sample to results obtained from investigating of a thin film present on a sample with a substantially smooth surface, there are different ways to proceed. One involves the case where an uncoated, textured or rough surface of a substrate is accessible by a beam of electromagnetic radiation, (eg. for instance, on the back of a sample substrate). In this case a preliminary measurement can taken from this uncoated surface. The measurement should be taken using the same measurement conditions, (eg. angle of incidence, wavelength range, and sample orientation including any special tip-tilt to align pyramid facets), as will be used for investigating a coated substrate. That is, the correction has been shown to vary with measurement conditions, so a distinct correction is needed if the measurement conditions are varied. After measurement of the substrate, the correction is calculated empirically by modeling the sample as combination of:

1) ideal substrate; and 2) correction factor or matrix.

Characterization of the ideal substrate is calculated using Fresnel interaction with the optical model of the known substrate which is calculated from the substrate optical constants, and any known surface layers. The correction factor or correction matrix is then allowed to "fit" to match up with the experimental measurement taken from the rough or textured surface. The correction factor or correction matrix can consist of:

i. a Real term which is multiplied by the ideal sample matrix;

ii. Both Real and Imaginary terms which are multiplied by the ideal sample matrix.

iii. a 2×2 Jones matrix of terms that are multiplied by the ideal sample matrix; and iv. a 4×4 Mueller matrix of terms that are multiplied by the ideal sample matrix.

Once the empirical correction is determined, its values are fixed to use with modeling of a coated substrate, from which data is obtained under the same measurement conditions. Note, in this situation, the ideal sample matrix is modified to include the coating properties, (eg. film thickness and optical constants).

In the case wherein an uncoated substrate is not available, the same method described above could be applied to a substrate coated with "known" thin film. The ideal sample matrix would then be modified to include the effects of the "known" thin film.

An alternate method to this approach would be to fit both the uncoated and coated samples using a "multi-sample" analysis method to determine one consistent correction matrix or correction factor. This method could also be applied to samples where a bare substrate is not available, but multiple coated substrates are available.

For reference, for an isotropic sample where rp and rs are the Fresnel reflection coefficients for p- and s-polarized light, the governing equation is:

$$\tan(\Psi) \cdot e^{i\Delta} = \frac{r_p}{r_s}$$

Also, the Jones Matrix for an ideal sample is:

$$\begin{pmatrix} r_p & 0 \\ 0 & r_s \end{pmatrix}$$

and the equation which describes the interaction of p and s light with an ideal isotropic sample is:

$$\begin{pmatrix} p_{out} \\ s_{out} \end{pmatrix} = \begin{pmatrix} r_p & 0 \\ 0 & r_s \end{pmatrix} \cdot \begin{pmatrix} p_{in} \\ s_{in} \end{pmatrix}$$

In the case where a macroscopically rough sample scatters away p- and s-light in different ways, the equation becomes:

$$\begin{pmatrix} p_{out} \\ s_{out} \end{pmatrix} = F \cdot \begin{pmatrix} r_p & 0 \\ 0 & r_s \end{pmatrix} \cdot \begin{pmatrix} p_{in} \\ s_{in} \end{pmatrix}$$

and the "effective" Psi ($\psi$) and Delta ($\Delta$) values measured become:

$$\tan(\Psi_{eff}) \cdot e^{i\Delta_{eff}} = F \cdot \frac{r_p}{r_s}$$

where rp and rs are the ideal Fresnel coefficients.

It is also possible that a rough surface can cross-scatter light from p- to s-components, and vice versa. This is accounted for by a scattering matrix "S":

$$\begin{pmatrix} p_{out} \\ s_{out} \end{pmatrix} = \begin{pmatrix} S_{pp} & S_{sp} \\ S_{ps} & S_{ss} \end{pmatrix} \cdot \begin{pmatrix} r_p & 0 \\ 0 & r_s \end{pmatrix} \cdot \begin{pmatrix} p_{in} \\ s_{in} \end{pmatrix}$$

The elements of the "S matrix are in general complex, and it can be of benefit to normalize said "S" matrix. In this case the Psi ($\psi$) and Delta ($\Delta$) values measured are:

$$\tan(\Psi_{eff}) \cdot e^{i\Delta_{eff}} = \frac{r_p \cdot S_{pp} + r_s \cdot S_{pp}}{r_p \cdot S_{ps} + r_s \cdot S_{ss}}$$

Further, if the rough surface both cross-scatters and depolarizes a beam, then a Mueller matrix Scattering matrix can be defined. For an ideal isotropic sample the Mueller matrix is:

$$\begin{pmatrix} 1 & -N & 0 & 0 \\ -N & 1 & 0 & 0 \\ 0 & 0 & C & S \\ 0 & 0 & -S & C \end{pmatrix}$$

$$N = \cos(2\Psi)$$
$$C = \sin(2\Psi)\cos(\Delta)$$
$$S = \sin(2\Psi)\sin(\Delta)$$

and an equation which corrects for both cross-scattering and depolarization is:

$$MM_{eff} = SM \cdot \begin{pmatrix} 1 & -N & 0 & 0 \\ -N & 1 & 0 & 0 \\ 0 & 0 & C & S \\ 0 & 0 & -S & C \end{pmatrix} =$$

$$\begin{pmatrix} SM_{11} & SM_{12} & SM_{13} & SM_{14} \\ SM_{21} & SM_{22} & SM_{23} & SM_{24} \\ SM_{31} & SM_{32} & SM_{33} & SM_{34} \\ SM_{41} & SM_{42} & SM_{43} & SM_{44} \end{pmatrix} \cdot \begin{pmatrix} 1 & -N & 0 & 0 \\ -N & 1 & 0 & 0 \\ 0 & 0 & C & S \\ 0 & 0 & -S & C \end{pmatrix}$$

(Note, in the foregoing, "F", "SM" and "MMeff" stand for "Correction Factor", "Scattering Matrix" and "Effective Mueller Matrix", respectively).

The present invention is then a method of improving the accuracy of determining characterizing ellipsometric parameters for samples with non-ideal surfaces in that reflections therefrom comprise a significant non-speculalar component, comprising the steps of:

a) providing an ellipsometer system which comprises:
 a polarization state generator;
 a stage for supporting a sample;
 a polarization state detector; and
 a computer system.

The method continues with:

b) placing a sample having a non-ideal surface, said sample comprising a selection from the group consisting of:
 a bare surface;
 a surface comprising a thin film coating thereupon;
 a surface comprising a thin film coating thereupon of a known thickness;
on said stage for supporting a sample in a known orientation, and causing said polarization state generator to direct a polarized beam of electromagnetic radiation so that it impinges on a non-ideal surface of said sample resulting in significant non-specular reflection, and then enters the polarization state detector, such that ellipsometric data is acquired.

The method further comprises:

c) proposing a mathematical model for the sample in the known orientation thereof, said mathematical model being expressable as a matrix which relates orthogonal components of the beam which is provided by the polarization state generator and which is caused to impinge on the non-ideal surface of the sample, to those determined by the polarization state detector, and said mathematical model further comprising a correction factor or scattering matrix comprising elements, which correction factor or scattering matrix at least partially corrects for errors in the determination of said ellipsometric parameters which characterize said sample because the surface thereof is non-ideal;

d) applying said computer system to regress said mathematical model in step b onto the data provided by the polarization state detector in step c;

to the end that parameters in the mathematical model are evaluated.

(Note, where a thin film is present on the surface in step b, its thickness is preferably determined in a preliminary step, and its value fixed in the step c mathematical model. This leads to better values being determined for the correction factor. An alternative approach involves obtaining data from multiple samples that have different thin film thicknesses, made from the same material, then, in step d, simultaneously regressing onto the multiple samples simultaneously).

Said method then involves said determined correction factor value or scattering matrix elements values being fixed in said mathematical model, and further comprises:

e) providing an alternative sample having a non-ideal surface in that reflections therefrom comprise a significant non-specularal component, which has a thin film coating thereupon, said non-ideality corresponding to that of the sample in step b, and placing it upon said stage for supporting a sample in the same orientation as was the sample in step b, then causing said polarization state generator to direct a polarized beam of electromagnetic radiation so that it impinges on said non-ideal surface of said sample and then enters the polarization state detector, such that ellipsometric data is acquired;

f) proposing the same mathematical model for the alternative sample in the known orientation thereof, as was proposed in step c, said mathematical model being expressable as a matrix which relates orthogonal components of the beam which is provided by the polarization state generator and which is caused to impinge on the non-ideal surface of the sample, to those determined by the polarization state detector, and said mathematical model further comprising said fixed value correction factor or scattering matrix elements comprising elements, which correction factor or scattering matrix elements at least partially corrects for errors in the determination of said ellipsometric parameters which characterize said sample because the surface thereof is non-ideal.

The method then comprises:

g) applying said computer system to regress said mathematical model in step f onto the data provided by the polarization state detector in step e, to the end that characterizing parameters for alternative sample thin film are determined and are at least partially corrected for the effects of said alternative sample non-ideality.

A modified method can involve step b being practiced at least twice using at least two different samples which have different thicknesses of thin film on the surfaces thereof. When this is done, step c can involve simultaneous regression of the same mathematical model onto the at least two resulting data sets, such that the value of said correction factor or values of said scattering matrix elements are produced.

It is noted that the resulting correction factor or scattering matrix can be a correction factor which is a real or complex number, or a scattering matrix.

It is also noted that where the correction factor or scattering matrix is a scattering matrix, the entries of which are determined by repeating steps a-c a plurality of times on a plurality of samples which are substantially similar to that initially investigated in step a and which are oriented substantially identically thereto, and wherein at least one thereof has a thin film coating thereupon which is made of the same material as that of the sample investigated in step a, it is noted that the different thickness thereof on the surfaces allow said scattering matrix entries to be evaluated by simultaneously regressing data acquired for each of the plurality of samples onto mathematical models therefore. This is because correlation between thickness and refractive index of a thin film is broken by the simultaneous regression technique. The at least two samples can both have thin films on their surfaces, or at least one can have no thin films are made of the same material Especially important cases provide that:
a scattering matrix is present in the mathematical model and has two rows and two columns, (ie a Jones matrix); or
a scattering matrix is present in the mathematical model and has four rows and four columns, (ie. a Mueller matrix).

In any of the above recitations, it is to be understood that the ellipsometer system computer system can not only perform mathematical regressions, but also the operation of the polarization state generator and detector. Further, it is again noted that any of the methods disclosed herein can further include performing at least one selection from the group consisting of:
storing at least some data provided by said data detector in machine readable media;
analyzing at least some of the data provided by said data detector and storing at least some of the results of said analysis in machine readable media;
displaying at least some data provided by said data detector by electronic and/or non-electronic means;
analyzing at least some of the data provided by said data detector and displaying at least some of the results of said analysis by electronic and/or non-electronic means;
causing at least some data provided by said data detector to produce a signal which is applied to provide a concrete and tangible result; and
analyzing at least some of the data provided by said data detector and causing at least some thereof to produce a signal which is applied to provide a concrete and tangible result.

The present invention will be better understood by reference to the Detailed Description Section of this Disclosure, in conjunction with the Drawings.

BRIEF DESCRIPTION OF THE DRAWINGS

FIGS. 4b1 and 4b2 show top and side views of a textured sample which comprises a surface with a multiplicity of faceted pyramid shaped structures, with FIG. 4b2 indicating facet texturing can be present on front and back of a sample.

FIG. 4b3 shows that the sample of FIG. 4b2 can have a thin film a front side thereof.

FIG. 5b shows how the vertically oriented stage of FIG. 5a comprises a stage frame, a stage rotation effecting means, and the stage per se.

FIG. 5c shows a perspective view of how the stage rotation effecting means and the stage per se. of FIGS. 5a and 5b can be rotated in the stage frame, FIG. 5d shows a side view of the system in FIG. 5c, with a sample mounted to the stage per se.

DETAILED DESCRIPTION

To provide insight to the present invention, the following material from pending application Ser. No. 12/315,898 is presented.

Figure 1:
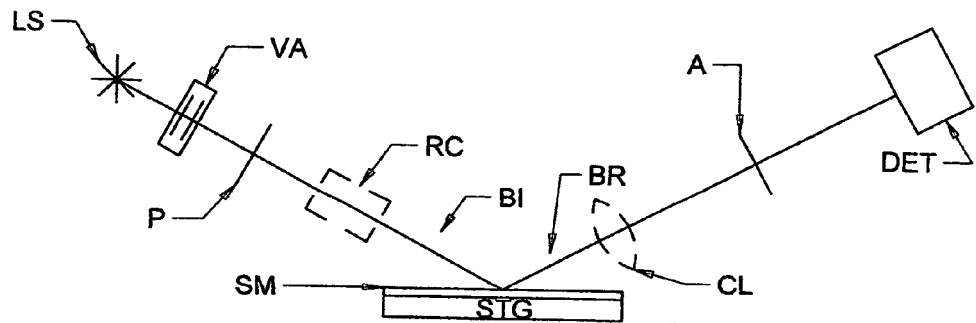
FIG. 1 shows a demonstrative ellipsometer system.

Turning now to FIG. 1, there is shown a basic well known demonstrative ellipsometer system comprising a Spectroscopic Source (LS) of a beam of electromagnetic radiation, a Variable Attenuator (VA), an optional Rotating Compensator, a Sample (SM) Stage (STG), an optional Collecting Means (CL), and Analyzer (A) and a Detector (DET). It is noted that the Variable Attenuator (VA) can be comprised of two polarizers which can be adjusted with respect to one another to control the intensity of electromagnetic radiation which passes therethrough.

Figure 2:
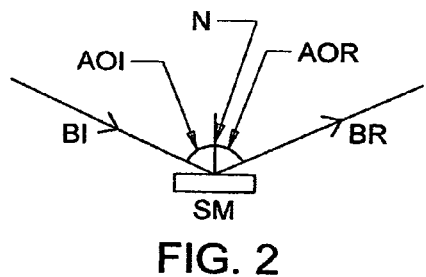
FIG. 2 shows an incident beam of electromagnetic radiation reflecting from a sample with a specular surface.

Continuing, FIGS. 1 and 2 show an Incident Beam (BI) of electromagnetic radiation reflecting as Reflected Beam (BR) from a Sample (SM) with a specular surface. Note that the Normal to the surface provides a reference for identifying Angle-of-Incidence (AOI) and Angle-of-Reflection (AOR). Note that a Plane-of-Incidence is defined as including both the locus of the Incident Beam (BI) and said Normal (N).

Figure 3A:
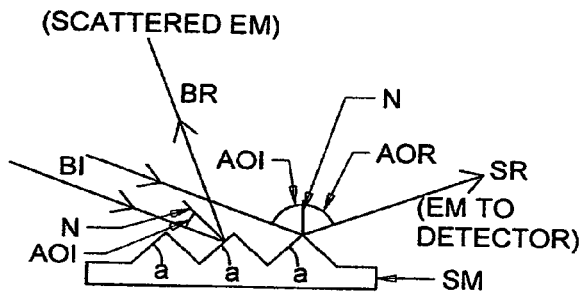
FIG. 3a is shows an incident beam of electromagnetic radiation reflecting from a sample with an irregular surface.
Figure 4A:
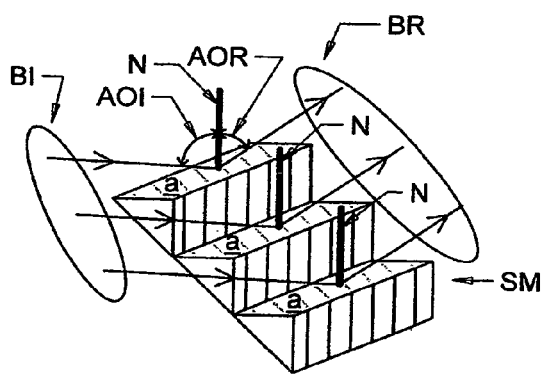
FIG. 4a showing the preferred textured sample orientation.
Figure 3B:
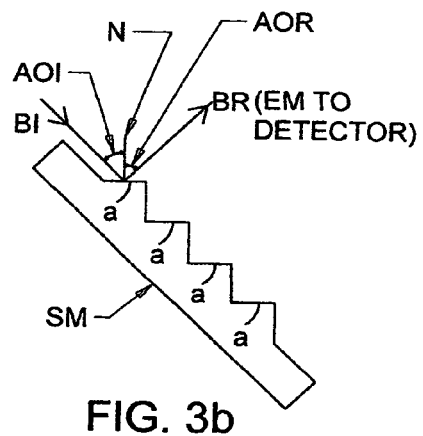
FIG. 3b shows a sample with an irregular surface oriented to increase the amount of electromagnetic radiation reflected therefrom toward a detector.

FIG. 3a shows an Incident Beam (BI) of electromagnetic radiation reflecting from a Sample (SM) with an irregular surface. Said FIG. 3a shows how the Normal (N) to the Sample (SM) surface varies in direction with position on said Sample (SM), such that electromagnetic radiation reflected at various locations proceed along different loci. Note that only a small amount of reflected electromagnetic radiation, from the peaks of the shown texture pattern, proceeds toward a Detector. This can lead to far to low an intensity entering the Detector to be analyzed. FIG. 3b shows how re-orienting the Sample (SM) in FIG. 3a can increase the amount of electromagnetic radiation reflected from facet (a) toward a Detector (DET) by presenting the breadth of—a—facet (a) to so direct reflected electromagnetic radiation. FIG. 4a shows how further re-orienting the Sample (SM) of FIG. 3b can greatly increase the amount of electromagnetic radiation reflected therefrom toward a Detector (DET) by positioning a plurality of facets (a) as shown to reflect electromagnetic radiation toward said Detector (DET).

Figure 4C:
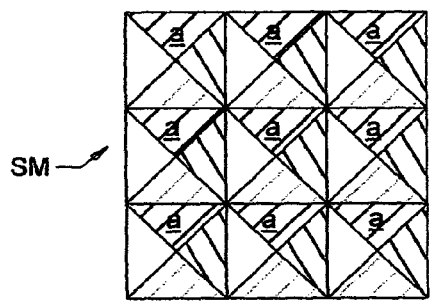
FIG. 4c shows how orienting the sample shown in FIGS. 4b1 and 4b2 much as the sample of FIGS. 3a and 3b is oriented in FIG. 4a can lead to increased reflected electromagnetic radiation reflected therefrom toward a detector.
Figure 4C:
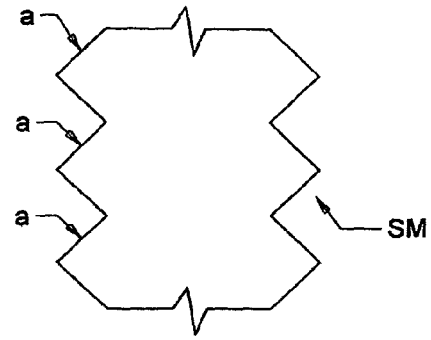
Figure 4C:
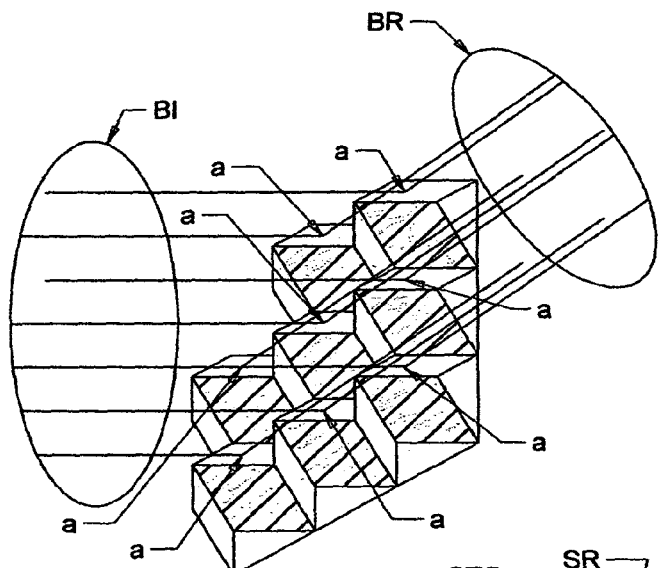

Note that the planes of the facets (a) in FIGS. 4a and 4c are substantially parallel to one another. This is important as electromagnetic radiation can simultaneously reflect from all such facets of a properly oriented sample, and enter the Detector (DET). This increases the intensity of the electromagnetic beam reflecting from said facets which enters the detector, which electromagnetic radiation can be analyzed as it is substantially similar, in important aspects, to specularly reflected electromagnetic radiation. As indicated in the Disclosure of the Invention Section of this Specification, achieving this result is a primary goal of the 898 Application invention. It is noted that simply adjusting the Angle-of-Incidence of a beam of electromagnetic radiation onto a textured surface of a sample, and adjusting the textured sample surface orientation can be undertaken with a goal of simply increasing intensity entering the Detector (DET), without regard to wherefrom on the textured sample surface reflection of electromagnetic radiation into the Detector (DET) occurs. This can lead to acquisition of data which can not be analyzed because too large a component of the electromagnetic radiation received by the Detector (DET) is noisy or depolarized etc. However, where essentially all reflected electromagnetic radiation is from substantially parallel facets, the data acquired is typically very good and its analysis can provide insightful information. It is also noted that if the textured surface of said sample is coated with a thin film, ellipsometric data obtained over a spectroscopic range of wavelengths can be analyzed to evaluate physical and optical properties of said thin film.

FIGS. 4b1 and 4b2 are included to show that a texture pattern can comprise other than grooves as shown in FIGS. 3a-4c, and show, respectively, top and side views of a Sample (SM) which comprises a textured surface with a multiplicity of faceted pyramid shaped structures, with FIG. 4b2 indicating facet texturing can be present on front and back of a sample. This can occur, for instance, where a Sample (SM) is placed into an anisotropic etch bath without protecting the back side thereof. As described in the Disclosure of the Invention Section, the 898 Application invention methodology can beneficially make use of data obtained from the backside of such a sample, in evaluating physical and optical properties of a thin film on the front side thereof. Note, data obtained from regions comprising and not comprising a thin film on the one side thereof, or obtained from different, but essentially similar samples which in combination provide both film present and absent regions can be used as well, and all said possibilities should be considered as functionally equivalent.

FIG. 4c shows how orienting the Sample (SM) shown in FIGS. 4b1 and 4b2 much as the Sample (SM) of FIGS. 3a and 3b is oriented in FIG. 4a can lead to increased reflected electromagnetic radiation reflected therefrom toward a detector. For emphasis, note that where a group of substantially parallel facets (a) on a textured Sample (SM) surface are oriented to provide optimum intensity of electromagnetic radiation reflecting therefrom into a Detector (DET) (eg. such as shown in FIGS. 4a and 4c), reflections from other facets which are not so oriented, and for that matter contacts and the like deposited onto the textured surface of the Sample (SM), are directed away from the Detector (DET). See FIG. 3a for instance, which indicates (Scattered) electromagnetic radiation (EM) which is directed away from a Detector (DET) and (EM to Detector) which is reflected thereinto. This is a beneficial result as it reduces scattered reflected components from entering the Detector (DET) and adversely affecting the data provided thereby because of entered noise and depolarizing effects etc.

Figure 3C:
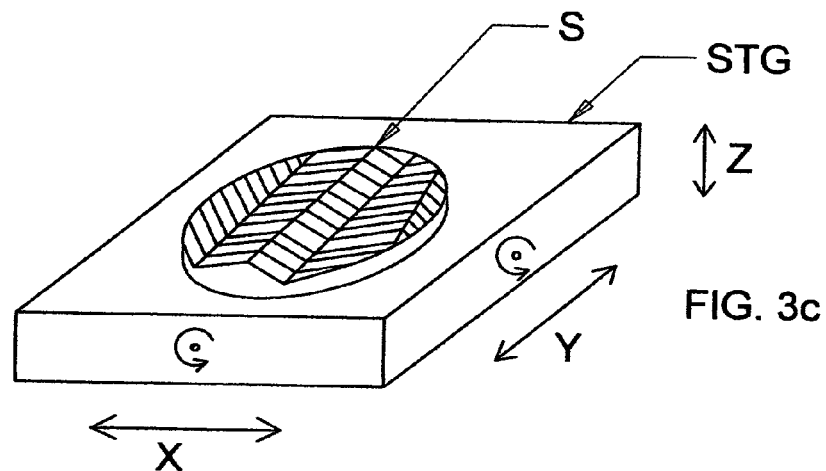
FIGS. 3c-3f are copied from U.S. Pat. No. 7,230,699 and show, respectively, a sample with an irregular surface, a means for orienting the sample of FIG. 3c, and how orienting said sample can control the Angle-of-Incidence to said sample, and therevia increase the amount of electromagnetic radiation reflected therefrom toward a location at which is positioned a detector by controlling the Angle-of-Incidence.
Figure 3D:
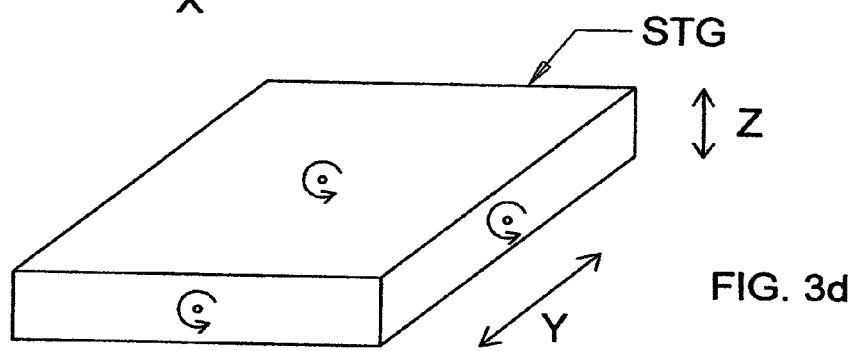
Figure 3E:
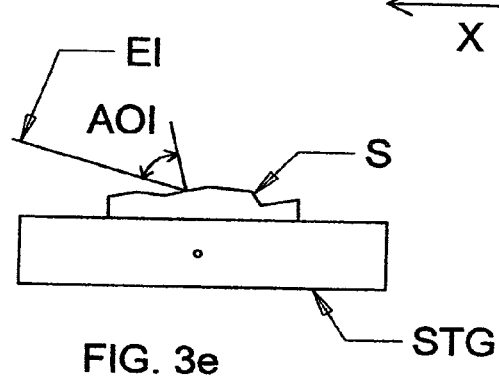
Figure 3F:
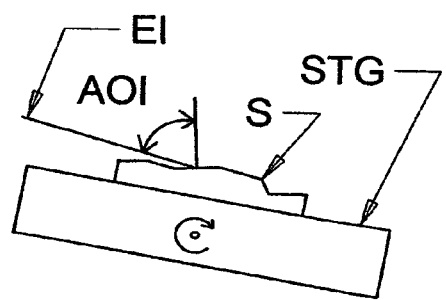
Figure 3G:
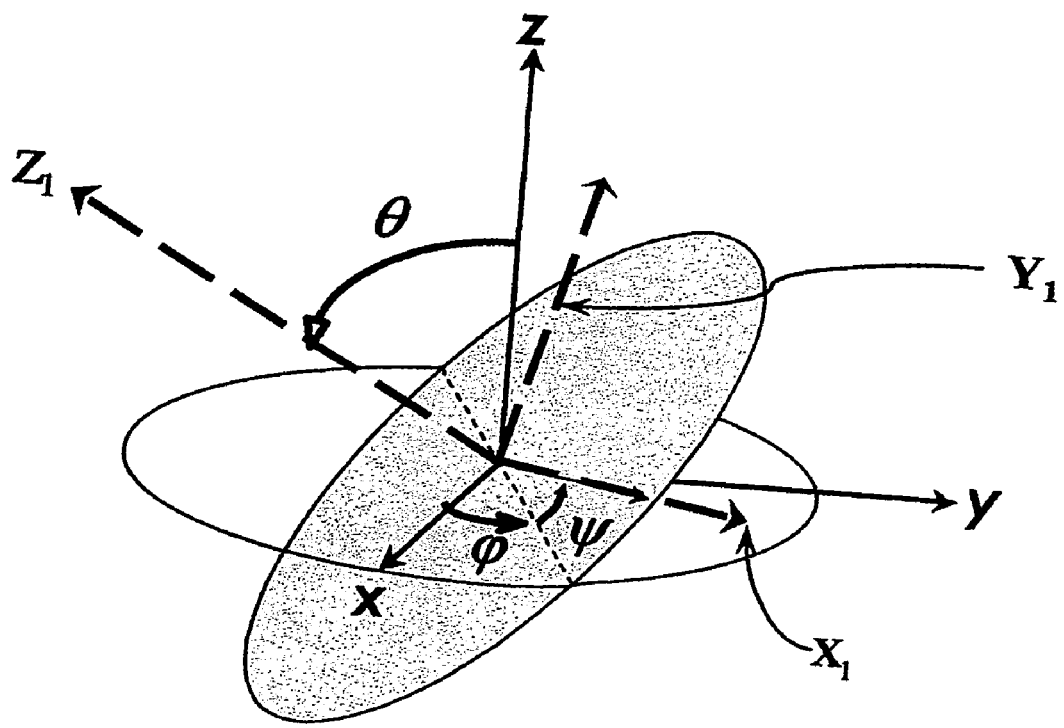
FIG. 3g demonstrates well known Euler Angles, which give insight to how the effect of tilting and rotating a sample can be described conventionally.

FIGS. 3c-3f are copied from U.S. Pat. No. 7,230,699 and are mentioned at this point to demonstrate priority provided by said 699 Patent via CIP status. FIG. 3c shows a sample (S) with an irregular surface. FIG. 3d shows a means (STG) for use in rotatably orienting the sample of FIG. 3c. FIGS. 3e and 3f show how orienting said sample can control the Angle-of-Incidence (AOI) to said Sample (S), and therevia increase the amount of electromagnetic radiation reflected therefrom toward a location at which is positioned a detector by controlling the Angle-of-Incidence (AOI). FIG. 3g is included to demonstrate well known Euler Angles Theta (θ), Phi (φ) and Psi (ψ), which give insight to how the effect of tilting and rotating a sample can be described conventionally. For instance, the Euler Theta (θ) describes Sample (SM) tilt with respect to a Stage (STG) Frame (SF) as said terminology is used herein, and the Euler Phi (φ) describes Sample (SM) rotation in the plane of the Sample (SM) surface.

Figure 5A:
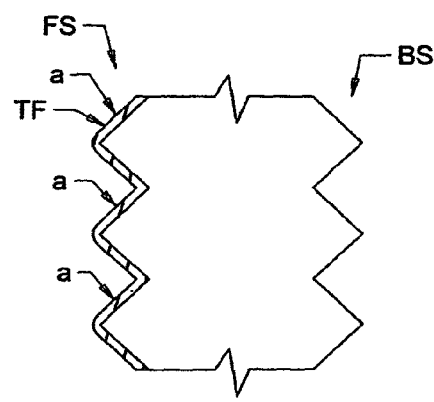
FIG. 5a shows an ellipsometer systems with the stage oriented vertically.
Figure 5A:
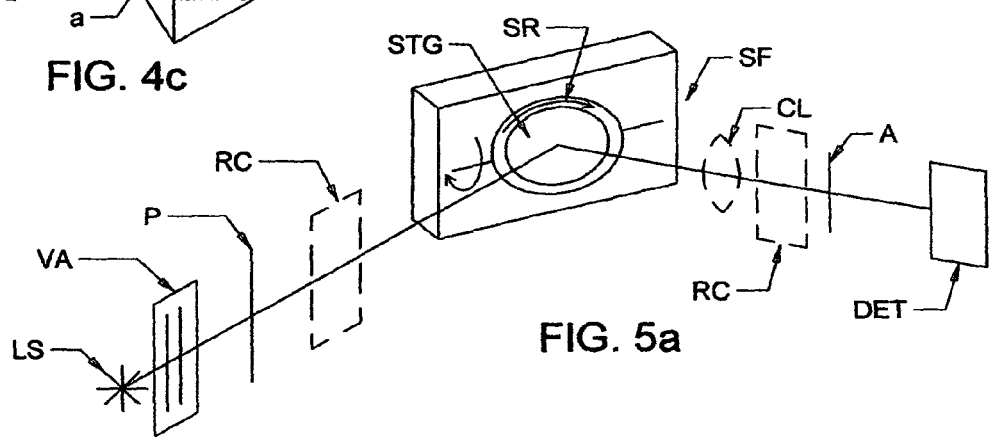

Continuing, FIG. 5a shows an ellipsometer system, much as shown in FIG. 1, but with the Stage (STG) oriented vertically, and being supported by a Stage Frame (SF) and Stage Rotation Means (SR). FIG. 5b better shows how the vertically oriented stage of FIG. 5a. FIG. 5c shows a perspective view of how the Stage (STG) Rotation Effecting Means (SR) and the Stage (STG) per se. of FIGS. 5a and 5b can be rotated in the Stage Frame (SF). FIG. 5d shows a side view of the system in FIG. 5c, with a Sample (SM) mounted to the Stage (STG) per se. Compare FIG. 5d with FIGS. 4a and 4c, with the assumption that the Incident Beam (BI) is approaching said Sample (SM) in a plane perpendicular to the plane of the paper. Note that both rotation of the Stage Rotation Means (RM) in the Stage Frame (SF), and rotation of the Stage (STG) in said Stage Rotation Means (RM) can be applied to optimally orient the Sample (SM) for ellipsometric investigation so that as much as is possible of electromagnetic radiation reflected from the Sample (SM) enters the Detector in FIG. 5a.

The described combination of a Stage Frame (SF), Stage Rotation Means (SR) and Stage (STG) as shown in FIGS. 5a-5d is believed not to have been previously applied in ellipsometer systems to orient textured Samples (SM) therein to enable ellipsometric investigation thereof, where said Sample (SM) orientation is demonstrated in FIGS. 4a and 4c, particularly in the case of where spectroscopic ellipsometry is practiced to investigate a Textured Sample (SM) over a spectrum of wavelengths. This is further the case where ellipsometric data obtained from, for instance, the backside of a Sample (SM) that has texturing on both the Front (FS) and backside (BS) (see FIG. 4b2), but also has a Thin Film (TF) being present only on the Front Side (FS) (see FIG. 4b3), is analyzed by using results obtained by investigating the Back Side (BS) in arriving at physical and optical properties of the Thin Film (TF) on the front side. Such a situation can present in Solar Cell Samples that have an anti-reflective coating on the Front Side (FS) thereof, for instance.

Figure 5E:
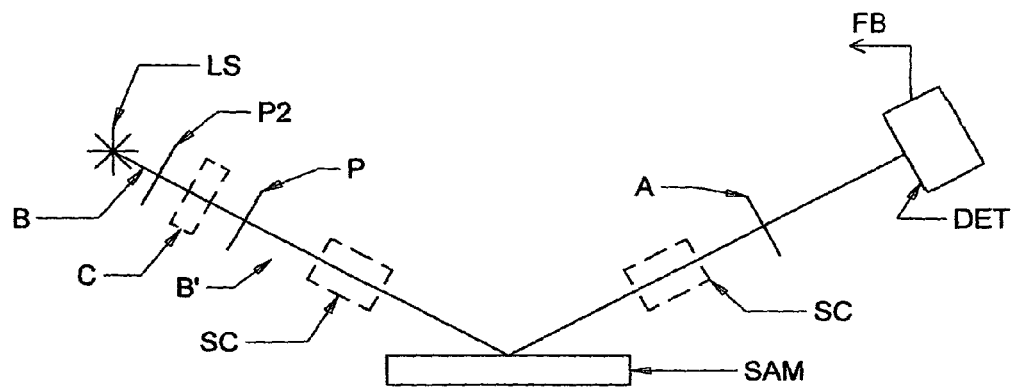
FIG. 5e shows a system for controlling the intensity of a beam of electromagnetic radiation comprising a Source (LS) of a Beam (B) of Electromagnetism, a Control Polarizer (P2), an optional Control Compensator (C), a Beam Polarizer (P), a Sample (SAM), an Analyzer (A) and a Detector (DET).
Figure 5F:
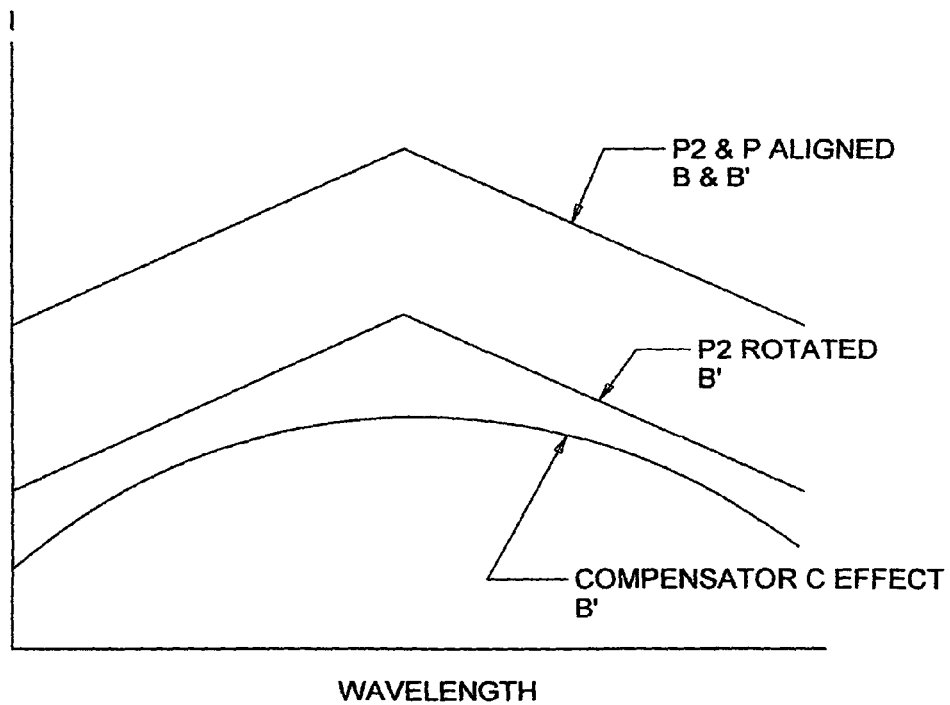
FIG. 5f shows an arbitrary demonstrative effect on Intensity (I) of a Beam (B') as compared to the Intensity of Beam (B) provided by a Source (LS) in FIG. 1.

FIG. 5e shows a Source (LS) of a Beam (B) of Electromagnetism, a Control Polarizer (P2), an optional Compensator (C), a Beam Polarizer (P), a Sample (SAM), an Analyzer (A) and a Detector (DET). FIG. 5f shows an arbitrary demonstrative effect on Intensity (I) of a Beam (B') as compared to the Intensity of Beam (B) provided by a Source (LS). Note the baseline Intensity (I) when said Control and Beam Polarizers (P2) and (P) aligned, and that rotating the Control Polarizer (P2) with respect to the beam Polarizer (P) has a uniform effect over the Wavelength Spectrum. Adding a Control Compensator (C) can cause selective increased attenuation of the mid-wavelength region and provide a more uniform Intensity Spectrum. Note also that at least one System Compensator (SC) can be incorporated into the system. (It is noted that where a Berek-type control compensator, which has its optical axis perpendicular to a surface thereof which a beam enters is used, the terminology "rotation" thereof should be interpreted to mean a tipping thereof to position the optical axis other than parallel to the locus of the beam which passes therethrough, and where the control compensator has its optical axis in the plane of a surface thereof which a beam enters is used, rotation should be interpreted to means an actual rotation about a perpendicular to said surface). It is disclosed that rotation of the control polarizer or compensator can be automated, optionally via a signal in a feedback circuit (FB).

It is noted that the direction of tilt-rotation shown in FIG. 5d can be considered to be positive or negative, and the 898 Application invention is sufficiently broad to include a corresponding negative or positive, respectively, tilt-rotation.

It is also noted that any type of ellipsometer or the like can be applied in practicing the methodology of the 898 Application invention, such as rotating polarizer, rotating analyzer, rotating compensator, or even phase modulation ellipsometers.

Figure 6A:
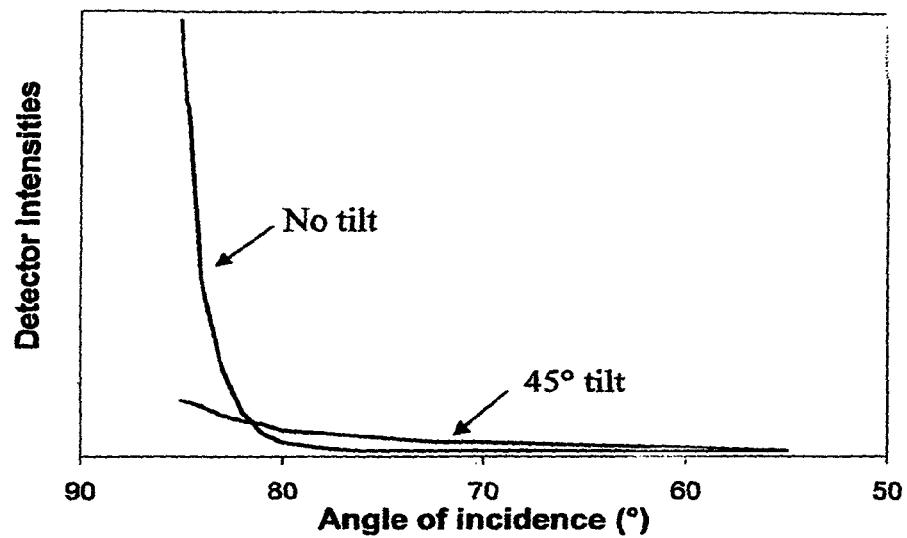
FIG. 6a demonstrates the effect of tilting a sample on intensity.
Figure 6B:
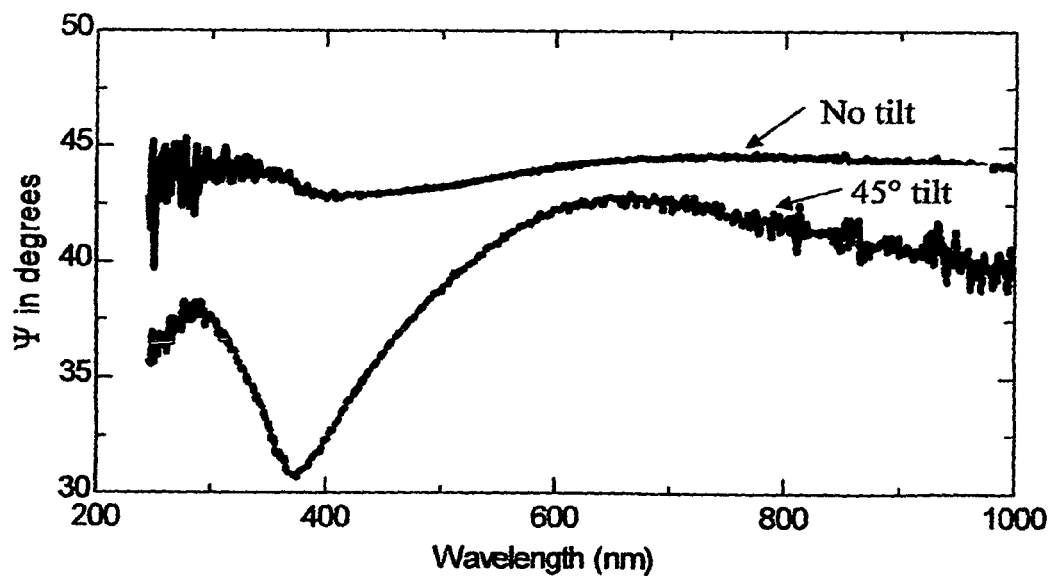
FIG. 6b demonstrates that even though intensity is reduced by sample tilt, the signal to noise ratio is improved.
Figure 6C:
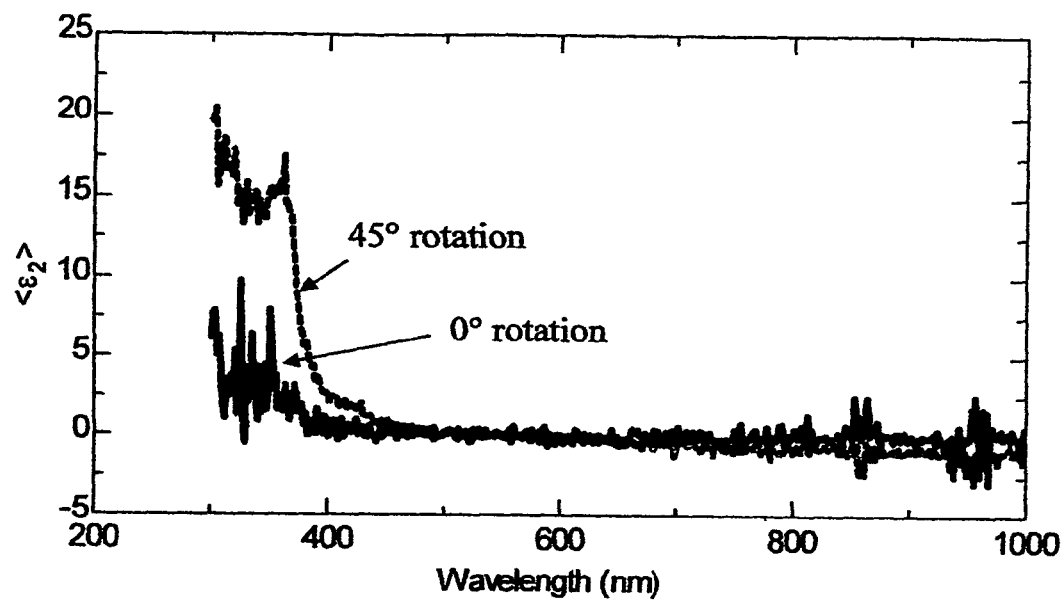
FIG. 6c shows that rotating a sample in the plane of the sample surface can improve the signal to noise ratio.
Figure 6D:
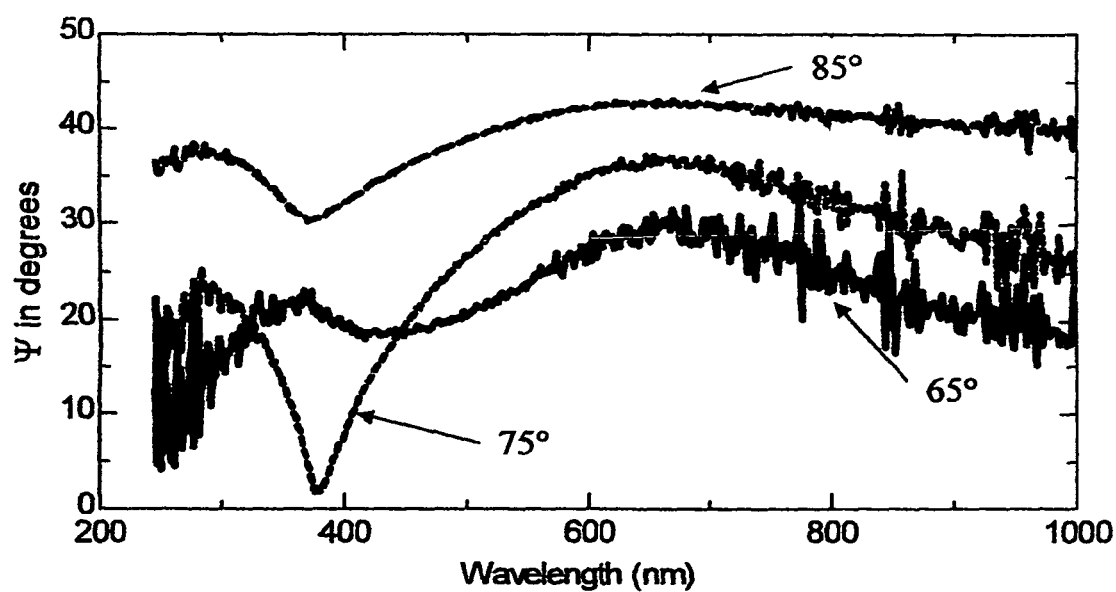
FIG. 6d demonstrates that Angle-of-Incidence can an effect on the signal to noise ratio.

Some exemplary experimentally acquired data is included, in FIGS. 6a-6d, to provide insight to results that were obtained by application of the 898 Application invention methodology. FIG. 6a demonstrates the effect of tilting a Textured Sample (SM) with respect to the Stage Frame (SF) plane, (as demonstrated by FIGS. 5c and 5d), on intensity as a function of Angle-of-Incidence (AOI). Note that the intensity a FIG. 5a Detector (DET) receives is significantly decreased by tilting a Sample (SM) by 45 degrees, with respect to the Stage Frame (SF) plane. This alone would not be beneficial, but FIG. 6b demonstrates that even though intensity is reduced by said Sample (SM) tilt, the shown PSI (ψ) signal to noise ratio, (as a function of wavelength), is greatly improved. This is because the diverted intensity reducing electromagnetic radiation is that which scatters from variously oriented facets as opposed to electromagnetic radiation which reflects from a multiplicity of facets which are parallel to one another. That is, even though less signal intensity arrives at the Detector (DET), the signal which is received by the Detector (DET) is of a higher quality, and when analyzed provides superior results. FIG. 6c further shows that rotating a titled Sample (SM), (with a textured surface), in the plane of the Sample (SM) surface, (see FIG. 5c), can also improve signal to noise ratio, (as a function of wavelength). FIG. 6d demonstrates that Angle-of-Incidence (AOI) can also have an affect on the signal to noise ratio in PSI ($\psi$) data, (as a function of wavelength). Note that at 65 degrees (AOI), as indicated by features of the plot, the data is noisy compared to the better defined PSI ($\psi$) data achieved at 75 and 85 degrees (AOI). (Note, data quality is indicated by enhanced data plot magnitude change vs. wavelength).

Finally, FIGS. 7a-7h provide sample data and fitting PSI and DELTA plots which demonstrate the important aspects of the present invention.

Figure 7A:
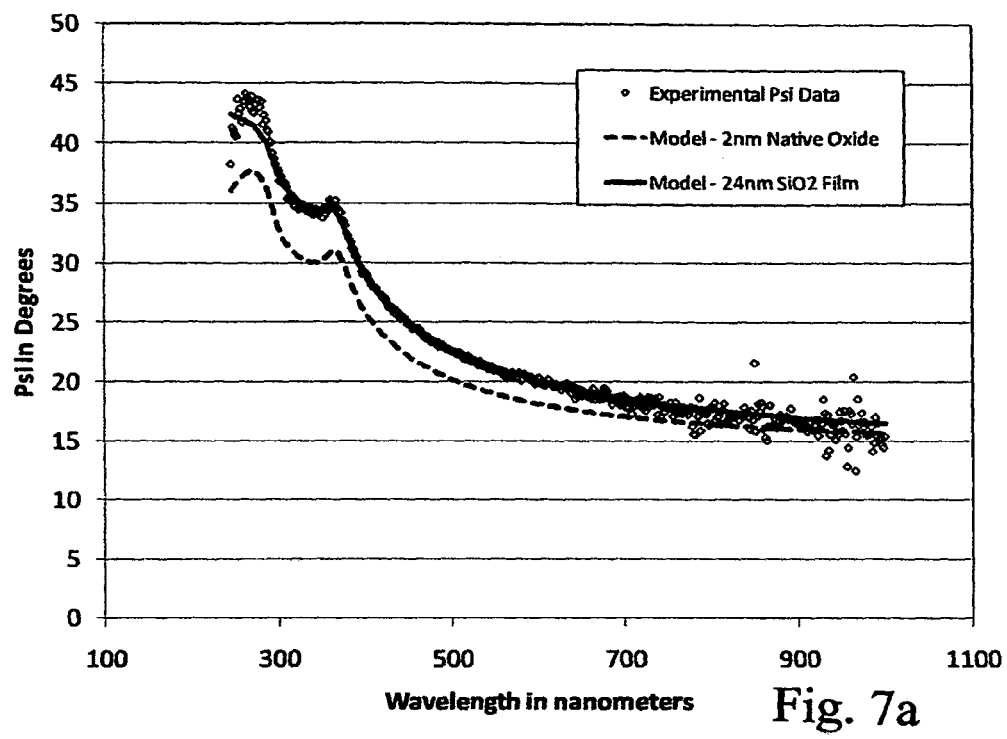
FIGS. 7a-7b show the need for including a Correction Factor in the Mathematical Model of a non-ideal Sample.
Figure 7B:
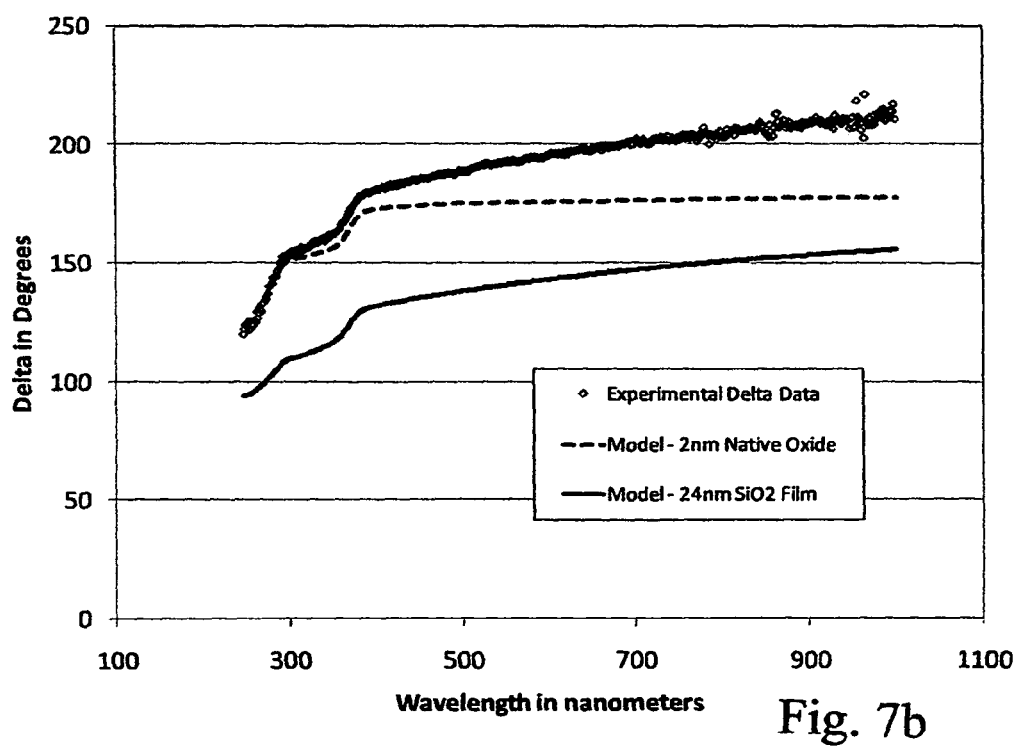

FIGS. 7a-7b are presented to demonstrate the need for a Correction Factor in the Mathematical Model of a Sample. Said plots show data for an uncoated silicon substrate with pyramidal texturing measured at 65 degree angle of incidence. For a polished substrate, the experimental data would easily be described using a model with silicon substrate optical constants and a thin native oxide (1-3 nm). As can be seen in the two graphs 7a and 7b, this native silicon model does not match actual Psi and Delta measurements. If the oxide thickness is presumed to vary, the best mode to match the Psi data occurs with 24 nm of SiO2. However, this can not be correct as the same model moves Delta further away from the experiment. Thus, this shows a correction is necessary to compensate the effect of the pyramidal texturing when applying the standard modeling approach for ideal samples.

Figure 7C:
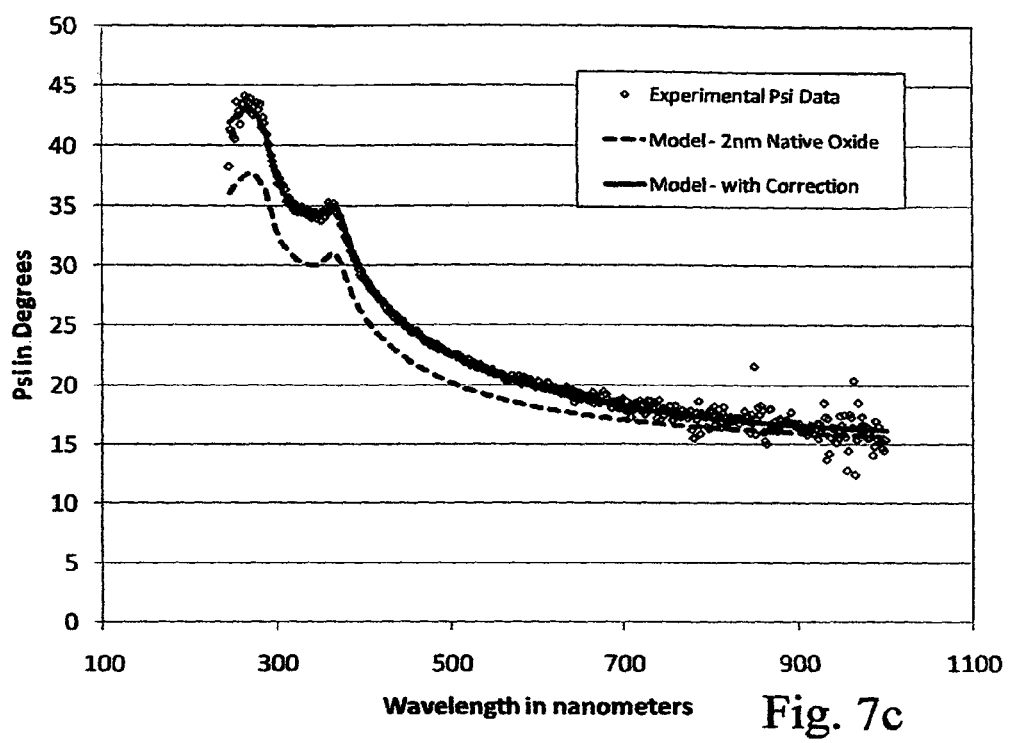
FIGS. 7c-7d show the effect of including a Scatter Matrix in the Mathematical Model of a Sample.
Figure 7D:
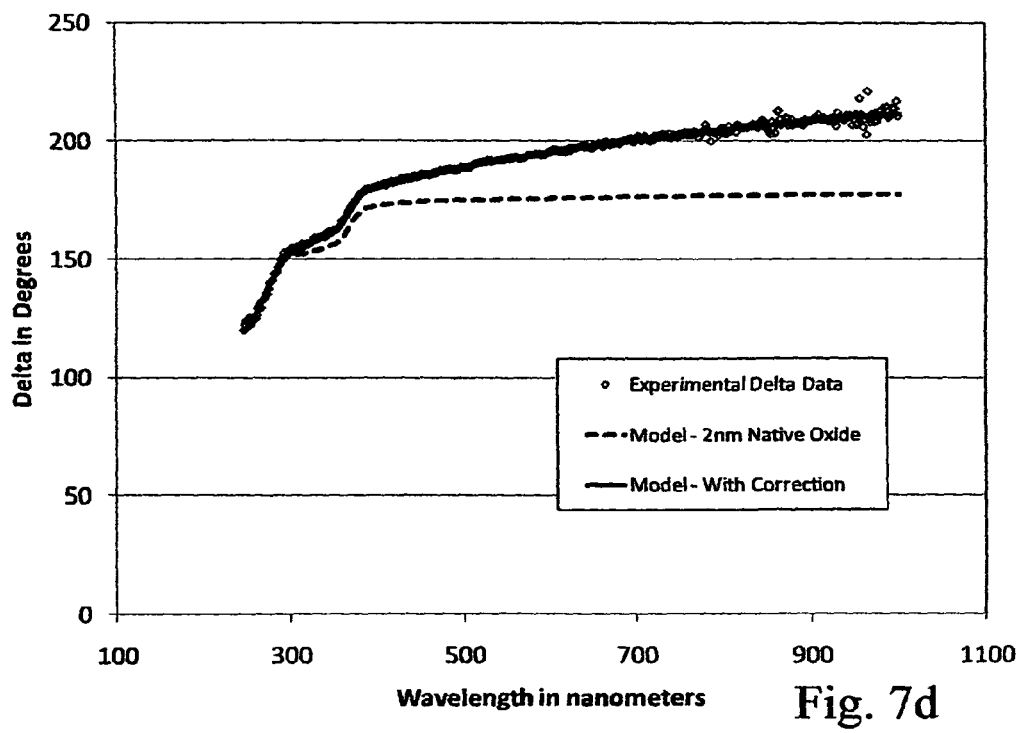
Figure 7E:
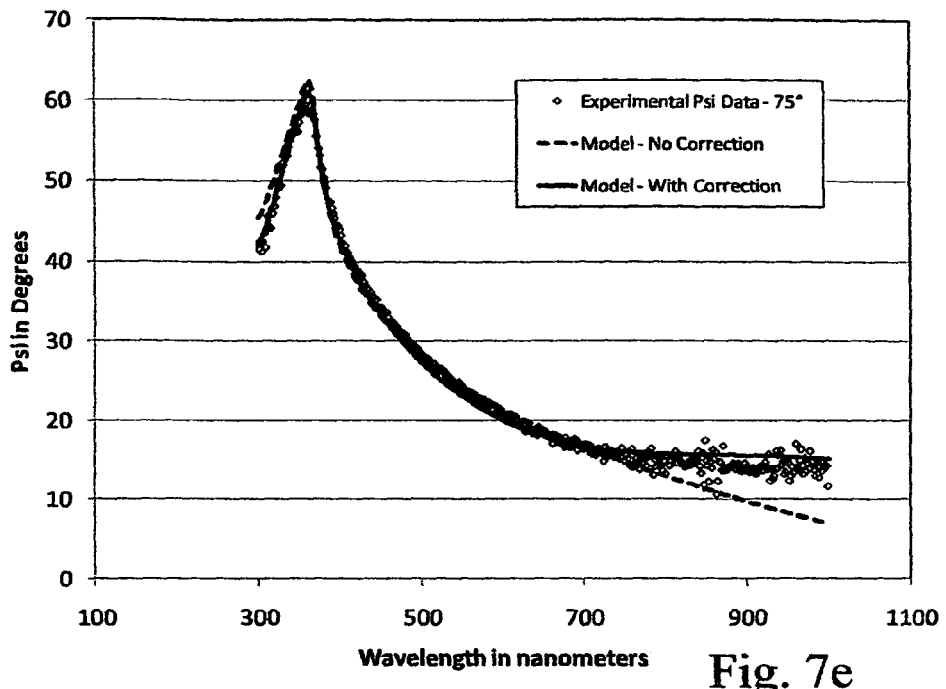
FIGS. 7e-7h show the effect of including a Correction Factor in Mathematical Models of Samples having different thicknesses of a thin film thereupon.
Figure 7F:
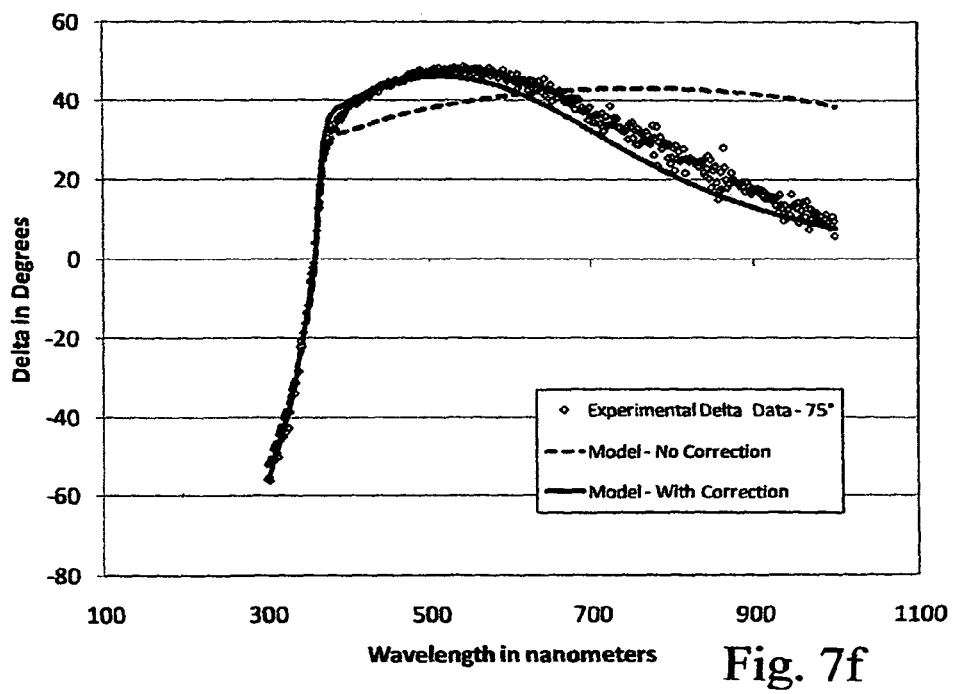
Figure 7G:
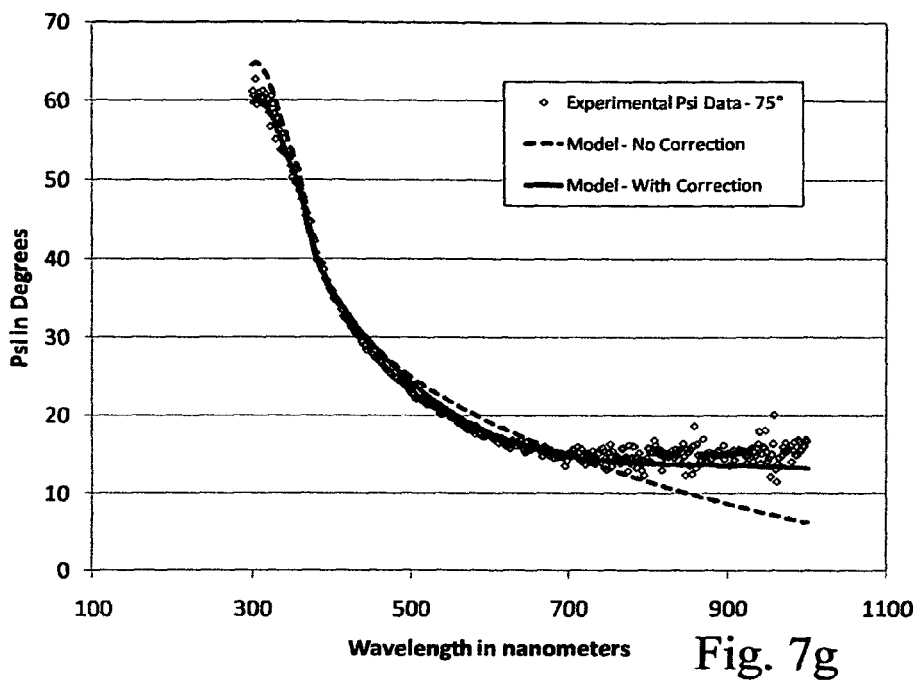
Figure 7H:
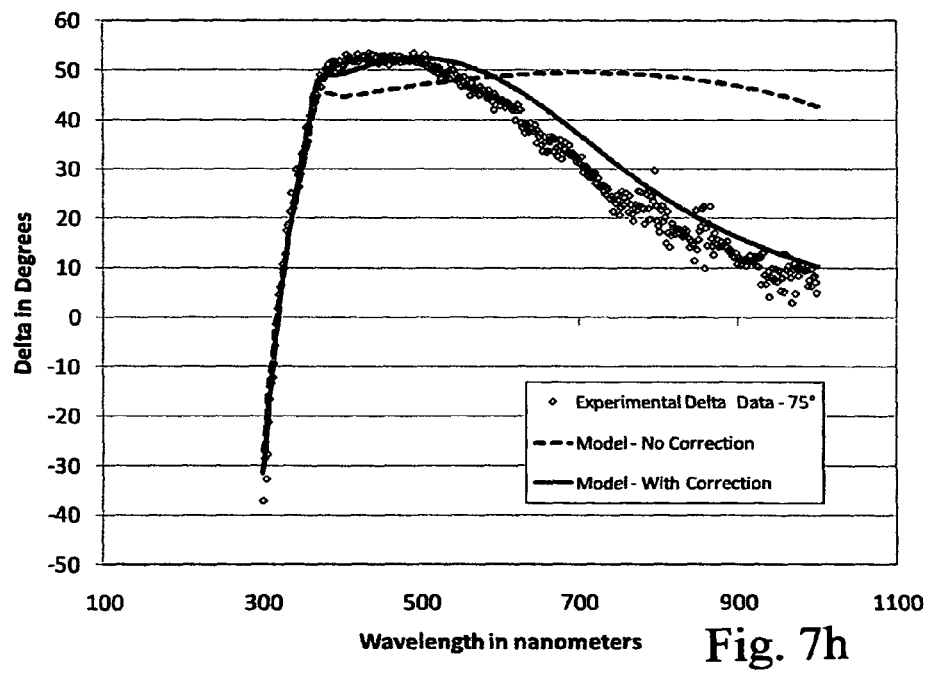

FIGS. 7c and 7d are presented to show the effect of including a Scatter Matrix correction in the Mathematical Model of a Sample. Data for uncoated, textured silicon can be described by adding a "correction matrix" that is multiplied by the ideal sample matrix for native-oxide coated silicon wafer. The match to the experimental data, both with (solid lines), and without (dashed lines), this correction matrix, is shown. This correction could then be used for additional samples to nominally extract results without the strong effects caused by the textured surface, provided the texturing is repeatable from sample-to-sample.

FIGS. 7e-7h show the effect of including a Correction Factor in Mathematical Models of Two Samples having different thicknesses of a thin film thereupon. For some samples it may not be possible to obtain an uncoated textured surface. In this case, the correction factor can be determined by using a multi-sample analysis where more than one sample with nominally the same coating, but different thickness thereof, are modeled using the same correction factor. Two data sets, (ie. for Sample 1 and Sample 2), for nitride-coated textured silicon are shown. The two nitride coatings are nominally the same as regards refractive index, but they have different film thickness on their surfaces. It is noted that data analysis involves use of simultaneous regression onto the two data sets corresponding to the two samples, which process breaks correlation between thin film thickness and refractive index for both. FIGS. 7e-7h data were first modeled without a correction factor, (see dashed lines). Next, both data sets for Samples 1 and 2 were fit simultaneously (multi-sample analysis) with a single correction factor to fit the underlying texture effects, (see solid lines). This provides consistent "correction" for similar samples of this coating on different substrates.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A computer controlled method of characterizing ellipsometric parameters for samples with non-ideal surfaces in that reflections therefrom comprise a non-specular component, comprising the steps of:
    a) said computer system controlling an ellipsometer system which comprises:
        a polarization state generator;
        a stage for supporting a sample;
        a polarization state detector; and
        said computer system;
    to acquire ellipsometric data from a non-ideal sample surface comprising:
        a bare surface;
        a surface comprising a thin film coating thereupon;
        a surface comprising a thin film coating thereupon of a known thickness;
    on said stage for supporting a sample in a known orientation, said computer system causing said polarization state generator to direct a polarized beam of electromagnetic radiation so that it impinges on a non-ideal surface of said sample resulting in non-specular reflection, and then enters the polarization state detector, such that ellipsometric data is acquired and saved;
    b) computer regressing saved data acquired in step a onto a mathematical model for the sample in the known orientation thereof, said mathematical model being expressed as a matrix which relates orthogonal components of the beam which is provided by the polarization state generator and which is caused to impinge on the non-ideal surface of the sample, to those determined by the polarization state detector, and said mathematical model further comprising a correction factor or scattering matrix comprising elements, which correction factor or scattering matrix at least partially corrects for errors in the determination of said ellipsometric parameters which characterize said sample because the surface thereof is non-ideal;
    to the end that parameters in the mathematical model are evaluated and tangibly presented by said computer.

2. A method as in claim 1 in which the value of said determined correction factor value or scattering matrix elements values are fixed in said mathematical model, and in which said method further comprises:
    c) said computer system causing investigation of an alternative sample having a non-ideal surface in that reflections therefrom comprise a non-specular component, which alternative sample has a thin film coating thereupon, said non-ideality corresponding to that of the sample in step a, then said computer system causing said polarization state generator to direct a polarized beam of electromagnetic radiation so that it impinges on said non-ideal surface of said alternative sample and then enters the polarization state detector, such that ellipsometric data is acquired and saved;
    d) computer regressing the saved data acquired in step c, onto the same mathematical model for the alternative sample in the same known orientation thereof as was applied in step b, said mathematical model being expressed as a matrix which relates orthogonal components of the beam which is provided by the polarization state generator and which is caused to impinge on the non-ideal surface of the sample, to those determined by the polarization state detector, and said mathematical model further comprising said fixed value correction factor or scattering matrix elements comprising elements, which correction factor or scattering matrix elements at least partially corrects for errors in the determination of said ellipsometric parameters which characterize said sample because the surface thereof is non-ideal;

to the end that characterizing parameters for alternative sample thin film are determined, are at least partially corrected for the effects of said alternative sample non-ideality and are tangibly presented by said computer.

3. A method as in claim 1, in which no thin film coating is present on the surface of the sample in step a.

4. A method as in claim 1, in which the thin film coating is present on the surface of the sample in step a, and its thickness is known and fixed in the mathematical model in step b.

5. A method as in claim 1, in which step a is practiced at least twice using at least two different samples which have different thicknesses of thin film on the surfaces thereof, and which involves said computer system performing simultaneous regression of the same mathematical model onto the at least two resulting data sets, such that the value of said correction factor or values of said scattering matrix elements are produced and presented by said computer in a tangible form.

6. A method as in claim 1 wherein the correction factor or scattering matrix is a correction factor which is a real or complex number.

7. A method as in claim 1 wherein the correction factor or scattering matrix is a scattering matrix.

8. A method as in claim 7, wherein the scattering matrix is present in the mathematical model and has two rows and two columns.

9. A method as in claim 7, wherein the scattering matrix is present in the mathematical model and has four rows and four columns.

10. A method as in claim 1 wherein the ellipsometer system computer system performs the mathematical regression in step b, as well as controlling the operation of the polarization state generator and detector in step a.

11. A method as in claim 1 wherein the correction factor or sattering matrix is a scattering matrix, and said scattering matrix entries are determined by repeating steps a and b a plurality of times on a plurality of samples which are similar, but wherein at least one thereof has a thin film coating thereupon which is made of the same material as that of another sample, but wherein said samples have different surface material thicknesses; said scattering matrix entries evaluation comprising simultaneously regressing data acquired for each of the plurality of samples onto mathematical models therefore by said computer.

12. A method as in claim 11, in which there are at least two samples in the plurality thereof which have a thin film coating thereupon which is made of the same material, but wherein each has a different thickness thereof on its surface; said scattering matrix entries evaluation comprising simultaneously regressing data acquired for each of the plurality of samples onto mathematical models therefore.

13. A method as in claim 11, in which at least one sample of the plurality thereof has no thin film coating on its surface, and another has thin film coating thereupon which is made of the same material and said scattering matrix entries evaluation comprises simultaneously regressing data acquired for each of the plurality of samples onto mathematical models therefore.

14. A method as in claim 11 wherein the ellipsometer system computer system in step a performs the both mathematical regression in step b as well as the operation of the polarization state generator and detector in step a.

\* \* \* \* \*